US010905823B2

(12) United States Patent
Constantineau et al.

(10) Patent No.: US 10,905,823 B2
(45) Date of Patent: Feb. 2, 2021

(54) SELF-CONTAINED SPRING INSERTER FOR DRUG DELIVERY INFUSION DEVICE

(71) Applicant: Becton, Dickinson and Company, Franklin Lakes, NJ (US)

(72) Inventors: Cole Constantineau, Cambridge, MA (US); Ryan Schoonmaker, Oceanside, CA (US); Azadeh Khanicheh, Newton, NJ (US); Michel Bruehwiler, Newton, NJ (US); Judy Walish, West Roxbury, MA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 251 days.

(21) Appl. No.: 15/917,442

(22) Filed: Mar. 9, 2018

(65) Prior Publication Data
US 2018/0193558 A1  Jul. 12, 2018

Related U.S. Application Data

(63) Continuation of application No. 14/678,732, filed on Apr. 3, 2015, now Pat. No. 9,943,643, which is a
(Continued)

(51) Int. Cl.
*A61M 5/158* (2006.01)
*A61M 5/142* (2006.01)
(Continued)

(52) U.S. Cl.
CPC .......... *A61M 5/158* (2013.01); *A61B 17/3415* (2013.01); *A61B 17/3496* (2013.01);
(Continued)

(58) Field of Classification Search
CPC .. A61M 2005/1585; A61M 2005/1586; A61M 25/0606; A61M 25/0631;
(Continued)

(56) References Cited

U.S. PATENT DOCUMENTS 3,918,355 A 11/1975 Weber
5,129,884 A 7/1992 Dysarz
(Continued)

FOREIGN PATENT DOCUMENTS

EP 2495001 A1 9/2012
JP 2005526560 A 9/2005
(Continued)

OTHER PUBLICATIONS

EPO, Communication in Application No. 12763545.6 pursuant to Rule 114(2) EPC, dated Jan. 4, 2018.
(Continued)

*Primary Examiner* — Quynh-Nhu H. Vu
(74) *Attorney, Agent, or Firm* — Dickinson Wright PLLC

(57) ABSTRACT

An infusion set includes a base (221) and a flexible catheter (242) movable from a first catheter position disposed substantially entirely within the base (221) to a second catheter position in which a free end of the catheter (242) is disposed externally of the base (221). An introducer needle (234) is located within the catheter (242) and is movable between a first introducer needle position disposed substantially entirely within the base (221) and a second introducer needle position in which a free end of the introducer needle (234) is disposed externally of the base (221). A spring (281) is activated to move the catheter (242) from the first to the second catheter position and the introducer needle (234) from the first to the second introducer needle position to facilitate insertion of the catheter (242). The introducer needle (234) is thereafter moved by the spring (281) back to the first introducer needle position to store the introducer needle (234) within the base (221) with the free end of the catheter (242) remaining disposed externally of the base (221).

13 Claims, 30 Drawing Sheets

Related U.S. Application Data continuation of application No. 13/983,992, filed as application No. PCT/US2012/000072 on Feb. 8, 2012, now Pat. No. 8,998,851.

(60) Provisional application No. 61/441,195, filed on Feb. 9, 2011.

(51) Int. Cl.
*A61M 25/06* (2006.01)
*A61B 17/34* (2006.01)

(52) U.S. Cl.
CPC .... *A61M 5/14248* (2013.01); *A61M 25/0606* (2013.01); *A61M 25/0631* (2013.01); *A61M 2005/1585* (2013.01); *A61M 2005/1586* (2013.01)

(58) Field of Classification Search
CPC .............. A61M 5/14248; A61M 5/158; A61M 2005/14506; A61M 5/1454; A61M 2005/202; A61M 5/3232; A61M 5/3257; A61M 2005/8281; A61M 2005/14252; A61M 2005/14284; A61M 2005/1583; A61M 5/162; A61M 2005/206; A61M 2005/3022; A61B 17/3415; A61B 17/3496

See application file for complete search history.

(56) References Cited

U.S. PATENT DOCUMENTS

| | | |
|---|---|---|
| 5,848,990 A | 12/1998 | Cirelli et al. |
| 6,485,461 B1 | 11/2002 | Mason et al. |
| 6,699,218 B2 | 3/2004 | Flaherty et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,303,549 B2 | 12/2007 | Flaherty et al. |
| 7,455,663 B2 | 11/2008 | Bikovsky |
| 7,682,338 B2 | 3/2010 | Griffin |
| 8,057,436 B2 * | 11/2011 | Causey ............. A61M 5/14244 604/151 |
| 8,512,287 B2 | 8/2013 | Cindrich et al. |
| 9,119,913 B2 | 9/2015 | Lanigan |
| 9,402,950 B2 | 8/2016 | Dilanni et al. |
| 2002/0022855 A1 | 2/2002 | Bobroff et al. |
| 2002/0040208 A1 | 4/2002 | Flaherty et al. |
| 2004/0010207 A1 | 1/2004 | Flaherty et al. |
| 2004/0162521 A1 | 8/2004 | Bengtsson |
| 2005/0171512 A1 | 8/2005 | Flaherty |
| 2005/0203461 A1 | 9/2005 | Flaherty et al. |
| 2006/0142698 A1 | 6/2006 | Ethelfeld |
| 2007/0027381 A1 | 2/2007 | Stafford |
| 2007/0093754 A1 | 4/2007 | Mogensen et al. |
| 2007/0219496 A1 | 9/2007 | Kamen et al. |
| 2007/0228203 A1 | 10/2007 | Ruff et al. |
| 2008/0195045 A1 | 8/2008 | Lanigan |
| 2008/0249473 A1 | 10/2008 | Rutti et al. |
| 2008/0312558 A1 | 12/2008 | Krulevitch et al. |
| 2008/0312588 A1 | 12/2008 | Faccioli et al. |
| 2009/0012472 A1 | 1/2009 | Ahm et al. |
| 2009/0062767 A1 | 3/2009 | Van Antwerp et al. |
| 2009/0099521 A1 | 4/2009 | Gravesen et al. |
| 2009/0198215 A1 | 8/2009 | Chong et al. |
| 2009/0254041 A1 * | 10/2009 | Krag ................. A61M 5/14248 604/180 |
| 2009/0306596 A1 | 12/2009 | Mogensen et al. |
| 2010/0100077 A1 | 4/2010 | Rush et al. |
| 2010/0274112 A1 | 10/2010 | Hoss et al. |
| 2010/0286714 A1 | 11/2010 | Gyrn et al. |
| 2011/0054285 A1 | 3/2011 | Searle et al. |
| 2011/0054390 A1 | 3/2011 | Searle et al. |
| 2011/0313357 A1 | 12/2011 | Skutnik et al. |
| 2014/0142508 A1 * | 5/2014 | Dilanni .................... F04B 9/02 604/151 |
| 2017/0128664 A1 | 5/2017 | Dilanni et al. |

FOREIGN PATENT DOCUMENTS

| | | |
|---|---|---|
| JP | 2006501878 A | 1/2006 |
| JP | 2006527036 A | 11/2006 |
| JP | 2008528086 A | 7/2008 |
| JP | 2008220961 A | 9/2008 |
| JP | 2009106749 A | 5/2009 |
| JP | 2009525822 A | 7/2009 |
| JP | 2009539444 A | 11/2009 |
| JP | 2010501281 A | 1/2010 |
| JP | 2010517700 A | 5/2010 |
| JP | 2010525869 A | 7/2010 |
| JP | 2010533525 A | 10/2010 |
| JP | 2010534530 A | 11/2010 |
| WO | WO-9620021 A1 | 7/1996 |
| WO | WO-02066093 A2 | 8/2002 |
| WO | WO-2004006982 A2 | 1/2004 |
| WO | WO-2004101071 A2 | 11/2004 |
| WO | WO-2006077262 A1 | 7/2006 |
| WO | WO-2008133702 A1 | 11/2008 |
| WO | WO-2008155377 A1 | 12/2008 |
| WO | WO-2009039013 A1 | 3/2009 |
| WO | WO-2012141759 A1 | 10/2012 |

OTHER PUBLICATIONS

EPO Communication in Application No. 12763545.6 pursuant to Article 94(3) EPC, dated Mar. 12, 2018.

* cited by examiner

SELF-CONTAINED SPRING INSERTER FOR DRUG DELIVERY INFUSION DEVICE

CROSS REFERENCE TO RELATED APPLICATIONS

This is a continuation of U.S. patent application Ser. No. 14/678,732 entitled "Self-Contained Spring Inserter for Drug Delivery Infusion Set" filed Apr. 3, 2015, which is a continuation application of U.S. patent application Ser. No. 13/983,992, filed Oct. 18, 2013, which is the U.S. national stage of International Application No. PCT/US2012/000072, filed Feb. 8, 2012, which claims the benefit under 35 U.S.C. § 119(e) of U.S. Provisional Application Ser. No. 61/441,195, filed Feb. 9, 2011, the entire disclosures of all of said prior applications being incorporated herein by reference.

FIELD OF THE INVENTION

The present invention relates generally to a drug delivery infusion set having a self-contained inserter. More particularly, the present invention relates to a self-contained inserter in which the introducer needle is stored in a base after being withdrawn from an insertion site. Still more particularly, the present invention relates to a self-contained inserter in which the introducer needle and catheter are inserted at an insertion site and the introducer needle is withdrawn from the insertion site by the push of a button.

BACKGROUND OF THE INVENTION

A large number of people suffering from diabetes use some form of insulin therapy to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. Infusion pumps, although more complex than syringes and pens, offer the advantages of continuous infusion of insulin, precision dosing and programmable delivery schedules. This results in closer blood glucose control and an improved feeling of wellness.

The use of an infusion pump further requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive that retains the base on the skin during use. The hub or base may be applied to the skin manually or with the aid of a manual or automatic insertion device. Often, the insertion device is a separate, stand-alone unit that the user is required to carry and provide.

There are many available versions of infusion set, including steel cannula infusion sets and soft (flexible) catheter sets. Soft catheter sets are typically inserted into a patient manually with the aid of a steel introducer needle, which is later removed from the patient leaving the soft catheter in place. In another type of infusion set, as noted above, a mechanized inserter is used to insert the introducer needle and catheter, remove the introducer needle, or both. The introducer needle is completely removed from the infusion set before being connected to the insulin pump.

One problem associated with manually inserting and retracting the introducer needle is variability in the insertion and retraction force, speed, smoothness and angle. This variability can lead to an increased rate of catheter insertion failure.

Further, as noted above, the user typically must remove the introducer needle after inserting the cannula. This exposes the user to accidental needle sticks from handling the removed introducer needle.

To monitor blood levels, such as a blood glucose level, the user typically must use a separate device other than the infusion set. The user has to carry this separate device in addition to the infusion set to check and/or monitor one's blood level. Accordingly, a need exists for an infusion set that incorporates a sensor to measure blood levels and facilitate insertion of the sensor.

Accordingly, a need exists for an infusion set that facilitates insertion of the cannula, while reducing the number of components a user must carry and substantially preventing accidental needle sticks.

SUMMARY OF THE INVENTION

An object of the present invention is to provide an exemplary infusion set that includes an integral introducer needle to facilitate cannula insertion.

Another object of the present invention is to provide an infusion set having a self-contained introducer needle to facilitate cannula insertion and reduce the number of components a user must carry.

Another object of the present invention is to provide an infusion set in which insertion of the catheter and introducer needle and retraction of the introducer needle is automatic, thereby substantially eliminating variability from the process.

Another object of the present invention is to provide an infusion set having a self-contained introducer needle to substantially reduce the overall size of the infusion set.

Another object of the present invention is to provide an infusion set having an integrated sensor, such as a blood glucose sensor.

Another object of the present invention is to provide an infusion set in which separate, self-contained introducer needles facilitate cannula and sensor insertion.

In accordance with an exemplary embodiment of the present invention, a drug delivery infusion set houses and stores the introducer needle and the means to insert and retract the introducer needle. The catheter and introducer needle are self-contained within the body of the infusion set. The introducer needle is automatically and fully retracted with the self-contained inserter. Because the introducer needle is self-contained in the base of the infusion set, the user does not have to manually remove the introducer needle. Thus, user contact with the introducer needle is avoided, thereby preventing accidental introducer needle sticks.

In accordance with another exemplary embodiment of the present invention, a drug delivery infusion set houses and stores a cannula for drug delivery and a sensing element for continuously monitoring blood levels, both of which are self-contained within the body of the infusion set. The cannula and sensing element are both substantially simultaneously inserted in an injection site. The infusion set incorporates the sensing element therein, thereby reducing the amount of equipment a user needs to carry as well as reducing the number of procedures the user must perform.

These and other objects are substantially achieved by providing an infusion set having an integrated and self-contained inserter that inserts a catheter and withdraws the introducer needle of the infusion set, thereby reducing the number of components required to be carried by the user. Additionally, accidental introducer needle sticks are substantially prevented while providing a low profile infusion set.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numerals will be understood to refer to like parts, components and structures.

DETAILED DESCRIPTION OF THE EXEMPLARY EMBODIMENTS

The exemplary embodiments of the present invention described below provide a novel means of inserting a soft catheter into the skin. For example, exemplary embodiments of the present invention provide an integrated inserter that inserts a soft catheter into the skin and withdraws the introducer needle into a base of an infusion set, as shown in FIGS. 1-8, while maintaining a low profile infusion set.

Figure 1:
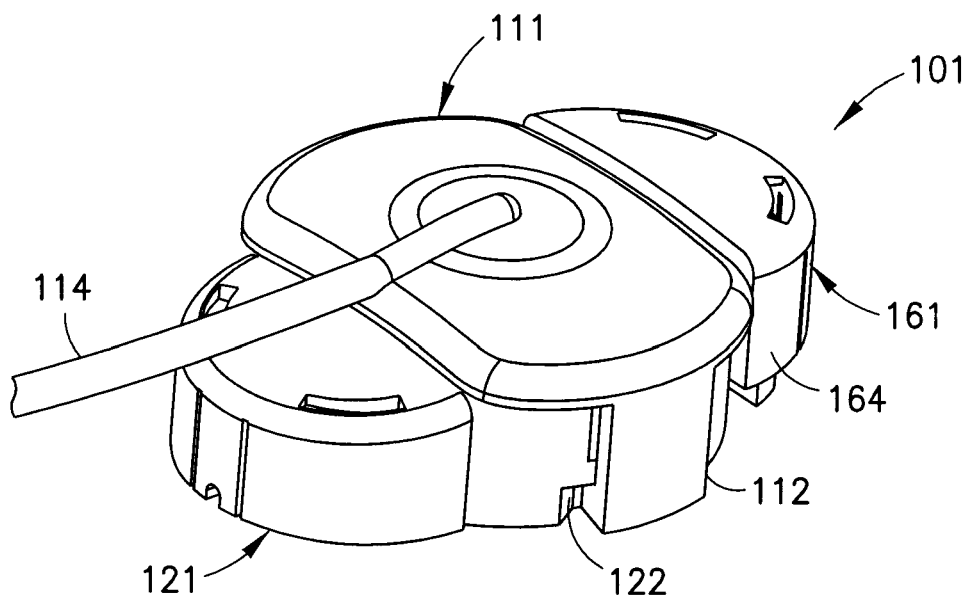
FIG. 1 is a perspective view of an assembled infusion set in accordance with a first exemplary embodiment of the present invention.
Figure 6:
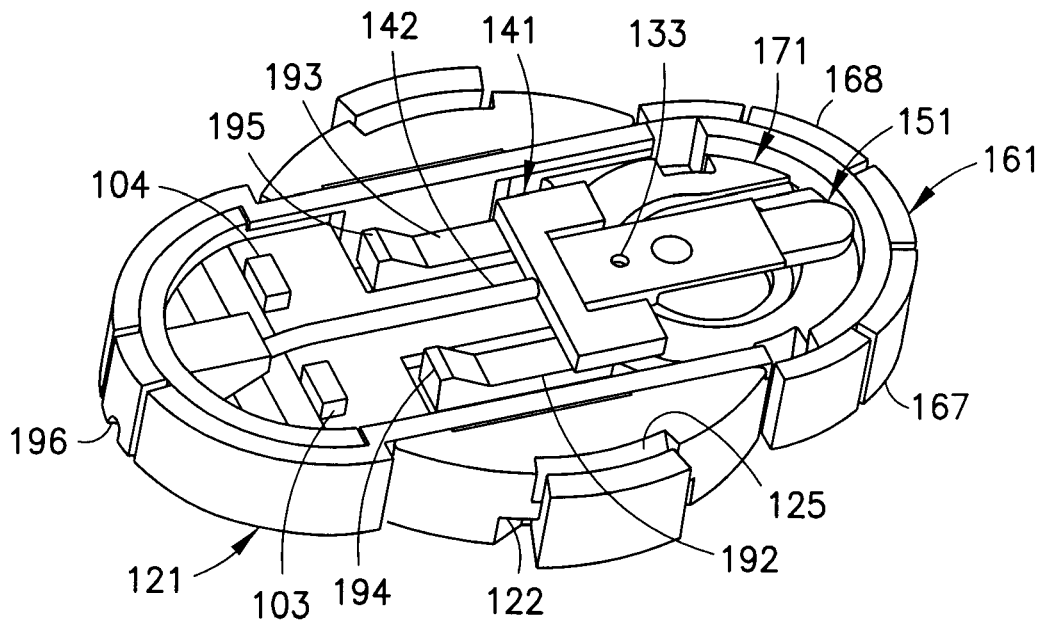
FIG. 6 is a partial perspective view of the infusion set of FIG. 1.
Figure 7:
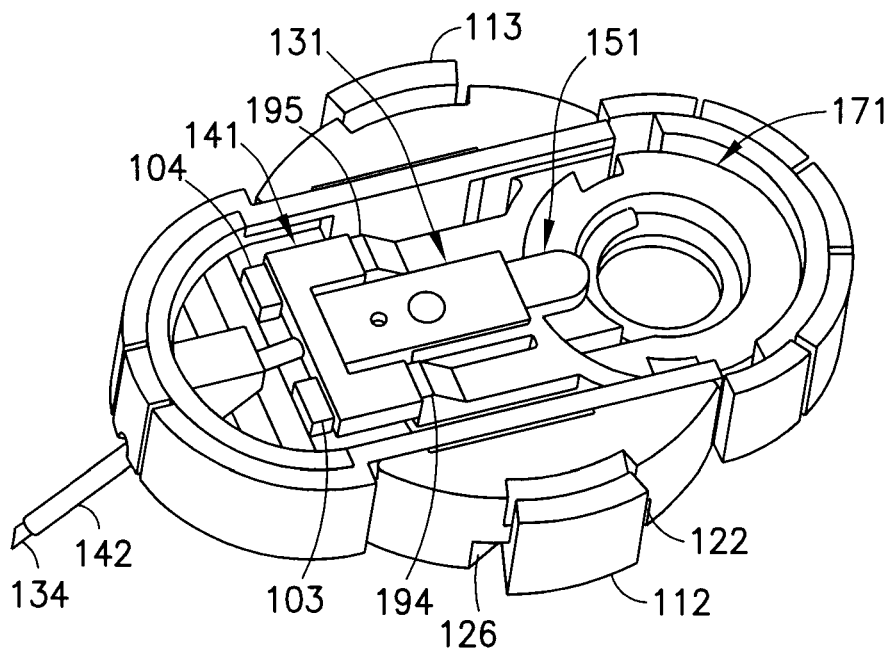
FIG. 7 is a partial perspective view of the infusion set of FIG. 1.

A base 121 of an infusion set 101, as shown in FIG. 1, is preferably provided with a skin-securing, adhesive layer (202 in FIG. 20) to secure the infusion set to the skin surface at a desired catheter insertion site. The adhesive layer ensures that the base is at the proper position relative to the skin surface, and that the skin is secured during insertion to further aid introducer needle insertion with a reduced risk of tenting of the skin surface. The base has a first recess 122 and a second recess (not shown) adapted to receive tabs of a fluid connector 111, thereby securing the fluid connector 111 to the base 121 to fully assemble the infusion set 101, as shown in FIG. 1. A first ramped surface 125 slopes downwardly and outwardly toward the first recess 122, as shown in FIG. 6, thereby facilitating the connector tab to slide down into the first recess and creating a snap-fit connection. Ramped surfaces 126 slope outwardly at opposite ends of the first recess 122, as shown in FIG. 7, thereby allowing the fluid connector 111 to be rotated with respect to the base 121 to allow the connector tabs to be released from the base recesses to disconnect the connector 111 from the base 121.

Figure 2:
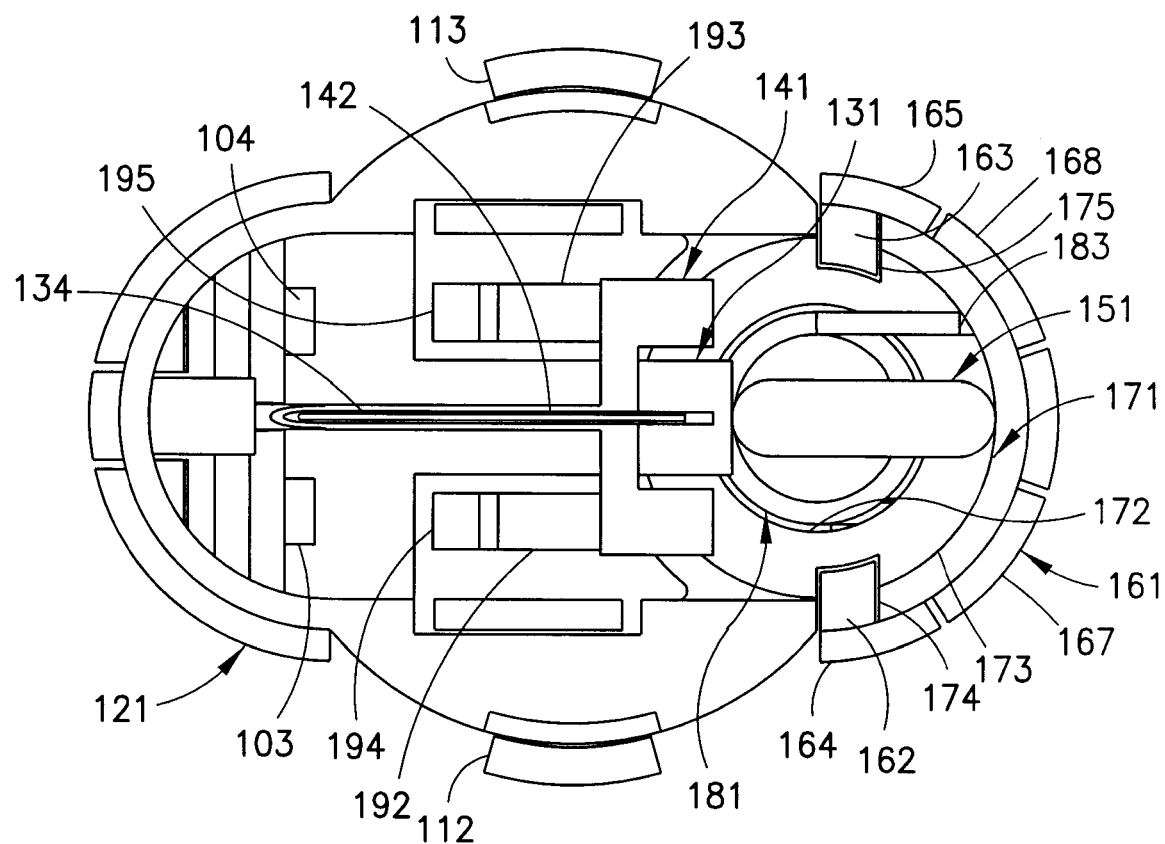
FIG. 2 is a top plan view in cross-section of the infusion set of FIG. 1.
Figure 3:
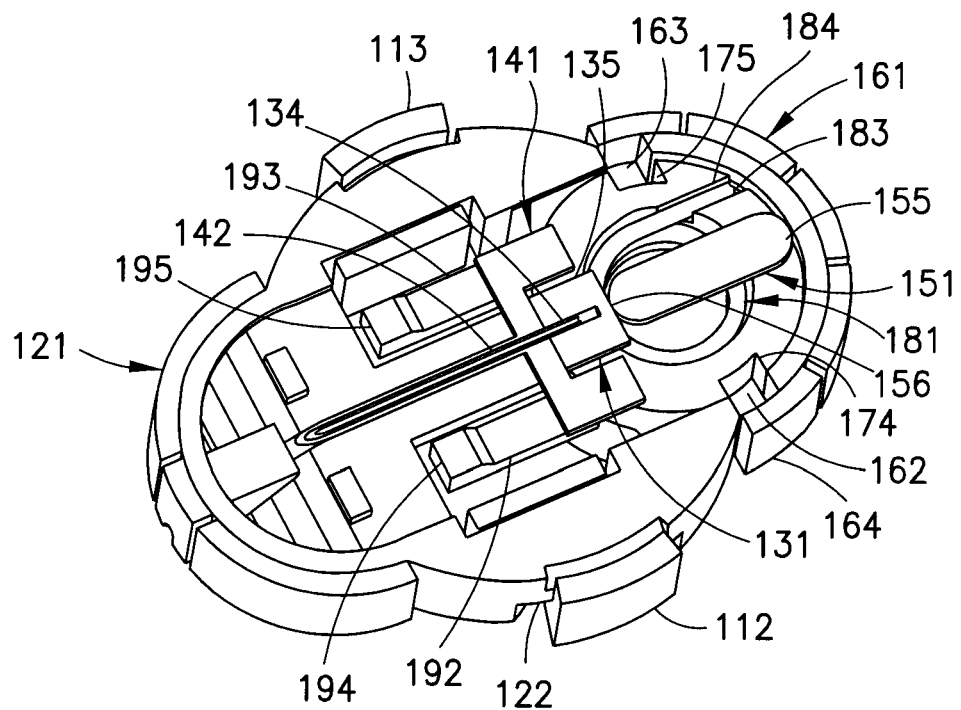
FIG. 3 is a partial perspective view of the infusion set of FIG. 1.
Figure 4:
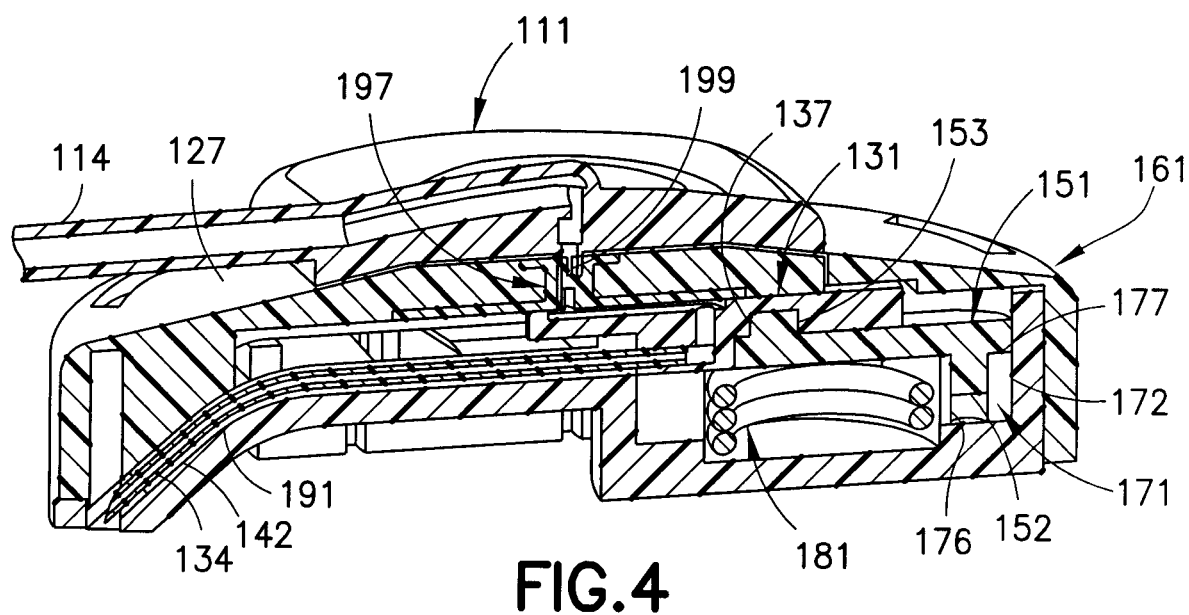
FIG. 4 is a side perspective view in cross-section of the infusion set of FIG. 1.
Figure 5:
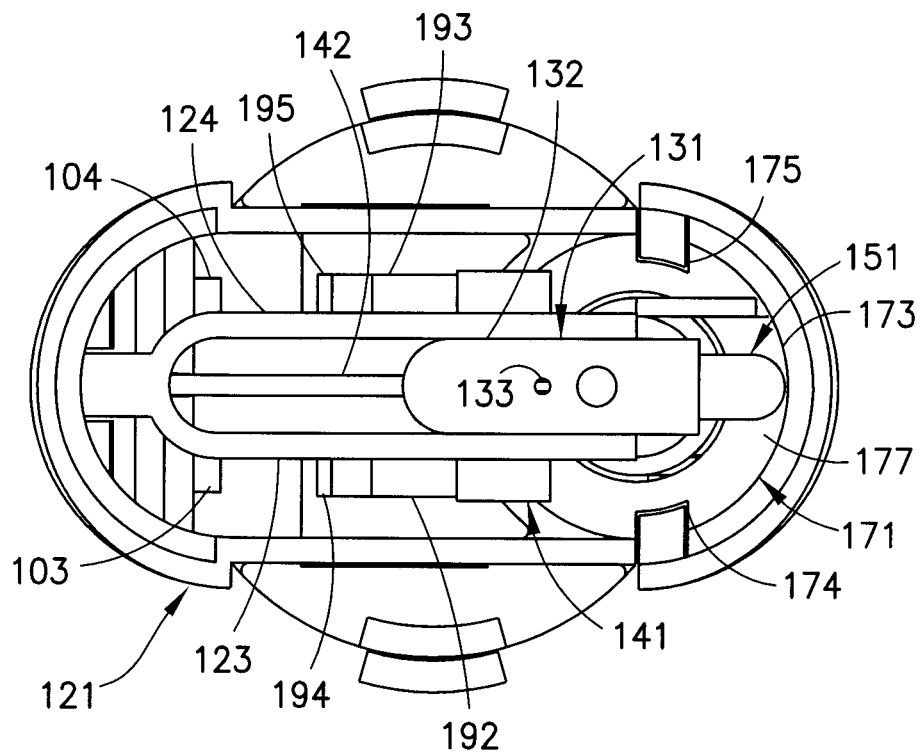
FIG. 5 is a partial top plan view of the infusion set of FIG. 1.

An introducer hub 131 is movably disposed in the base 121 of the infusion set 101, as shown in FIG. 2. An upper portion 132 of the introducer hub 131 has an opening 133 connected to a flexible introducer needle 134 rigidly connected to a lower portion 135 of the introducer hub 131, as shown in FIGS. 3 and 5. The upper portion 132 of the introducer hub 131 is disposed between guide rails 123 and 124 of the base 121, as shown in FIGS. 5 and 6, to guide linear movement of the introducer hub 131. The introducer hub 131 is movable from a first position shown in FIG. 5, to a second position shown in FIG. 7, and back to the first position shown in FIG. 5. When the introducer hub 131 is in the first position, the introducer needle 134 is disposed within the base 121 as shown in FIG. 4, thereby preventing any accidental introducer needle sticks. When the introducer hub 131 is in the second position, the introducer needle 134 is exposed outside of the base 121 as shown in FIG. 7 such that a patient's skin can be pierced to insert an angled catheter 142.

A catheter hub 141 abuts the lower portion 135 of the introducer hub 131, as shown in FIGS. 2 and 3. The flexible catheter 142 is rigidly connected to the catheter hub 141. The introducer needle 134 is movably disposed within the catheter 142, as shown in FIG. 4. Linear movement of the introducer hub 131 results in linear movement of the catheter hub because of the engagement the lower portion 135 of the introducer hub 131 and the catheter hub 141. The catheter hub 141 is movable between a first position shown in FIGS. 5 and 6, and a second position shown in FIG. 7. When the catheter hub 141 is in the first position, the catheter 142 is disposed within the base 121. When the catheter hub 141 is moved to the second position, the catheter 142 is moved out of the base 121 and is insertable at an angle under the surface of a patient's skin.

A disc 171 is rotatably disposed in the base 121, as shown in FIGS. 2-8. The disc 171 has an inner perimeter 172 forming an aperture therethrough and an outer perimeter 173. A torsion spring 181 is disposed within the inner perimeter 172 of the disc 171. Preferably, the torsion spring 181 is a 360 degree torsion spring, i.e., the torsion spring causes the disc 171 to rotate 360 degrees upon release. First and second recesses 174 and 175 are formed in the outer perimeter 173 of the disc 171. An opening 176 is formed in an upper surface 177 of the disc, as shown in FIG. 4 and receives a first protrusion 152 of a linking arm 151.

The torsion spring 181 has a first end rigidly fixed to the base 121. A second end 183 of the torsion spring 181 is fixed to the disc 171, as shown in FIGS. 2 and 3. An opening 184 can be formed in the disc 171 to receive the torsion spring.

The linking arm 151 connects the disc 171 to the introducer hub 131, thereby converting rotational movement of the disc 171 into linear movement of the introducer hub 131. The first protrusion 152 of the linking arm 151 extends downwardly proximal a first end 155 of the linking arm 151, as shown in FIGS. 3 and 4. A second protrusion 153 extends upwardly from a second end of the linking arm 151 and is received by an opening 137 in the introducer hub 131.

The button 161 is movable between a first, or up, position as shown in FIG. 1, and a second, or lower, position as shown in FIG. 4. Tabs 162 and 163 extend inwardly from free ends of arms 164 and 165 extending downwardly from an upper surface 166 of the button, as shown in FIGS. 1-3. When the button 161 is in the first position, as shown in FIGS. 1 and 2, the tabs 162 and 163 are received within the recesses 174 and 175 of the disc 171, thereby preventing rotational movement of the disc 171. When the button 161 is pressed downwardly to the second position, as shown in FIG. 3, the tabs 162 and 163 are moved downwardly below the disc 171 such that the tabs are no longer disposed in the disc recesses 174 and 175, thereby allowing the disc 171 to rotate due to the torque applied by the torsion spring.

Snap arms 167 and 168 extend downwardly from the button 161, as shown in FIGS. 2 and 6. Hooks disposed at the free ends of the snap arms 167 and 168 are received in upper recesses (not shown) in the base 121, thereby maintaining the button 161 in the up position shown in FIG. 1. When the catheter 142 is to be inserted, the button 161 is pushed downwardly to the second position and the snap arms 167 and 168 move from the upper recesses to lower recesses (not shown) in the base 121. The snap connection between the button snap arms 167 and 168 and the lower recesses in the base 121 maintains the button 161 connected to the base 121 after inserting the catheter 142.

An angled guide 191 is provided in the base 121 to guide movement of the introducer needle 134 and the catheter 142. The angled guide 191 creates an angle with respect to the surface of the skin of between approximately 30 and 45 degrees, inclusive, and preferably about 45 degrees. An opening 196 is formed in the base at the end of the angled guide 191 to allow the introducer needle 134 and catheter 142 to exit the base. First and second flexible arms 192 and 193 extend in the base 121 in the direction of movement of the catheter hub 141. Upwardly extending hooks 194 and 195 are disposed at an end of the flexible arms.

Figure 8:
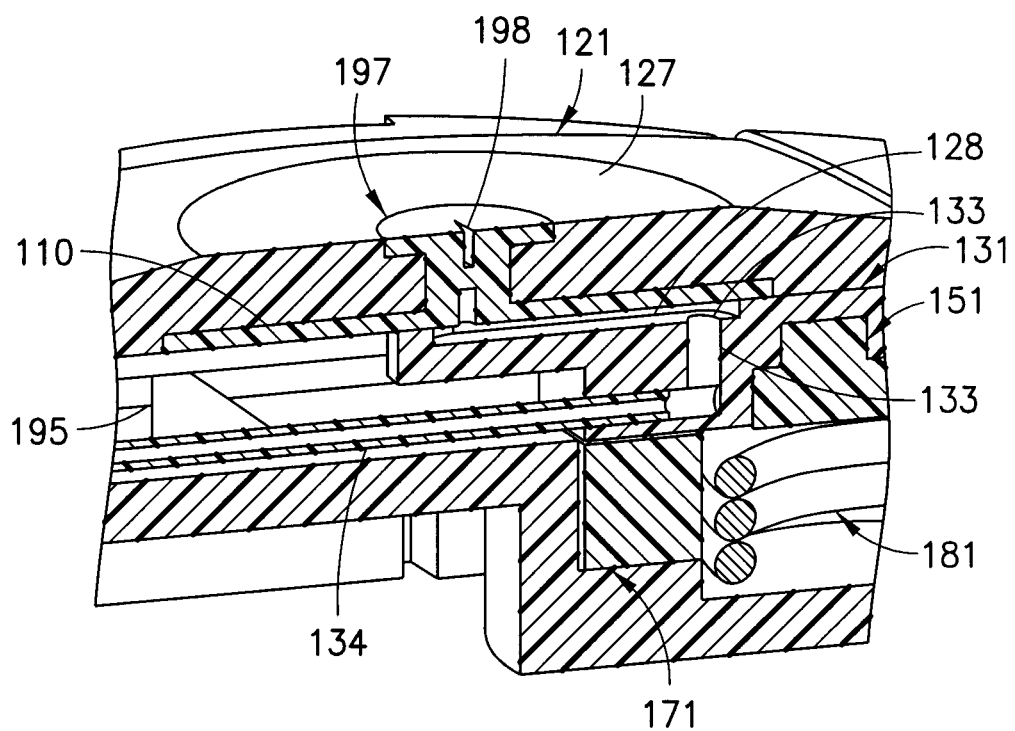
FIG. 8 is a partial perspective view in cross-section of the infusion set of FIG. 1.

A septum 197 is disposed in an upper surface 127 of the base 121, as shown in FIGS. 4 and 8. Preferably, the septum 197 has a slit 198 to facilitate receiving a penetrating member, or sharp, 199 of the connector 111, as shown in FIG. 4, although the slit may not be required in some cases. A groove 128 is formed in an upper surface of the introducer hub 131, as shown in FIG. 8, and having one end at the introducer hub opening 133.

The fluid connector 111 has first and second flexible arms 112 and 113, as shown in FIGS. 1-3, that engage the first and second recesses 122 in the base 121 to secure the connector to the base. Tubing 114 extends from the fluid connector 111 and is adapted to connect to a pump. The tubing 114 is connected to a penetrating member 199 extending downwardly from the fluid connector 111, and a fluid path is formed therebetween. The penetrating member 199 is adapted to penetrate the septum 197 when the fluid connector 111 is connected to the base 121, as shown in FIG. 4.

Assembly and Operation

FIG. 1 is a perspective view of the infusion set 101 ready to be inserted by a user. The fluid connector 111 is secured to the base 121 by engaging the hooks of arms 112 and 113 in the base recesses 122, as shown in FIGS. 1 and 3. Ramped surfaces 125 in the base 121 facilitate engaging the connector arms 112 and 113 with the base recesses 122.

The button 161 is in the up, or first, position, as shown in FIG. 1. In this position, the button tabs 162 and 163 are disposed in the disc recesses 174 and 175, thereby preventing rotation of the disc 171. The linking arm 151 is aligned with the longitudinal axis of the catheter 142, as shown in FIG. 2. The catheter hub 141 and the introducer hub 131 are disposed to the right of the base 121 spaced from the hooks 194 and 195 of the base flexible arms 192 and 193, as shown in FIGS. 2 and 3. The catheter 142 and the introducer needle 134 are disposed within the base 121, thereby substantially preventing accidental introducer needle sticks.

Adhesive backing (not shown) is removed from the base 121 to expose an adhesive layer (202 in FIG. 20) on a lower surface of the base, such that the base can be firmly secured to a desired location on the skin. To insert the catheter 142, the button 161 is pushed downwardly to a down, or second, position to release the torsion spring 181, thereby driving rotational movement of the disc 171. The downward movement of the button 161 moves the button tabs 162 and 163 out of the disc recesses 174 and 175, thereby freeing the disc 171 to rotate. The button snap arms 167 and 168 move from the upper recesses to the lower recesses in the base 121, thereby securing the button 161 to the base 121. The second end 183 of the torsion spring 181 rotates with the disc 171.

As the disc 171 begins to rotate counter-clockwise as shown in FIGS. 2, 3, 5 and 6, the linking arm 151 moves with the disc. The movement of the linking arm 151, in turn, results in linear movement of the introducer hub 131. The introducer hub 131 is limited to linear movement by the guide rails 123 and 124, as shown in FIG. 5. The linear movement of the introducer hub 131 pushes the catheter hub 141 from a position shown in FIG. 6 to a position shown in FIG. 7. The introducer hub 131 pushes the catheter hub 141 along the base flexible arms 192 and 193 such that the catheter hub 141 flexes the arms 192 and 193 downwardly to pass over the hooks 194 and 195. After the catheter hub 141 passes over the hooks 194 and 195, the hooks snap back up to prevent rearward movement of the catheter hub 141 back along the flexible arms 192 and 193. Stops 103 and 104 disposed in the base 121 prevent further forward linear movement by the catheter hub 141. Additionally, the forward linear movement of the catheter hub 141 and the introducer hub 131 results in forward movement of the catheter 142 and the introducer needle 134, respectively. The catheter 142 is fixedly attached to the catheter hub 141 and the introducer needle 134 is fixedly attached to the introducer hub 131. The angled guide 191 in the base guides the downwardly angled movement of the catheter 142 and introducer needle 134. The introducer needle 134 extends beyond the catheter 142 such that the introducer needle pierces the surface of the skin to allow the catheter to be inserted at an angle beneath the surface of the skin. The disc 171 has rotated approximately 180 degrees at this point.

As the disc 171 continues to rotate past the 180 degree point, the linking arm 151 causes the introducer hub 131 to move linearly rearwardly between the guide rails 123 and 124. The hooks 194 and 195 of the base flexible arms 192 and 193 prevent rearward movement of the catheter hub 141. The rearward linear movement of the introducer hub 131 pulls the introducer needle 134 out of the insertion site, leaving the catheter 142 inserted at an angle beneath the surface of the skin. As the disc 171 continues to rotate to the 360 degree point, the introducer needle 134 is withdrawn entirely into the base 121 of the infusion set 101. The torsion spring 181 can be pre-loaded such that the disc 171 does not rotate more than approximately 360 degrees. Additionally, a stop tab (not shown) can be disposed in the base that mates with a corresponding stop tab (not shown) on the disc to prevent the disc from rotating more than approximately 360 degrees. The infusion set 101 is now ready to begin infusing insulin.

A fluid path is created from the connector tubing 114, through the septum 197, into the groove 128 of the introducer hub 131, through the opening 133 in the introducer hub 131, into the introducer needle 134 and into the catheter 142, as shown in FIGS. 4 and 8. The groove 128 is completely sealed by a lower surface 110 of the septum 197, as shown in FIG. 8. Furthermore, the groove 128 is completely sealed by the lower surface 110 of the septum 197 over the entire range of motion of the introducer hub 131, thereby forming a dynamic seal.

The fluid connector 111 and tubing 114 can be easily removed by rotating the connector relative to the base 121. The hooks of the connector arms 112 and 113 slide along the ramped surfaces 126 of the base recesses 122, allowing the connector 111 to be easily disconnected from the base. The fluid connector 111 can then be reconnected when desired as described above.

The pre-loaded torsion spring 181, when released by the button 161, performs both the insertion and retraction of the introducer needle 134. Torsion springs can store a large amount of energy within a small and flat profile. This is facilitated by the 360 degree rotation of the disc 171 driven by the torsion spring 181. The first 180 degree rotation of the disc 171 inserts the introducer needle 134, and the second 180 degree rotation of the disc retracts the introducer needle completely into the base 121. The torsion spring 181 can be pre-loaded to not less than 180 degrees and up to approximately 360 degrees to perform the insertion and retraction of the introducer needle.

The linking arm 151 between the introducer hub 131 and the disc 171 produces a cyclical piston movement. By using a flexible or bending introducer needle 134 and an angled catheter 142, the infusion set can have a low profile. The angled guide 191 in the base 121 guides the introducer needle downwardly into the surface of the skin. Moreover, the only action required by the user to press the button 161 downwardly. The insertion of the introducer needle 134 and the catheter 142 and retraction of the introducer needle occurs automatically. Additionally, by only requiring the user to push the button 161 downwardly, the infusion set 101 can be positioned and used in hard to reach and awkward body locations.

The septum 197 is disposed approximately in the center of the base 121, thereby allowing multiple orientations when connecting the connector 111 to the base 121. The sliding septum design between the linearly moving introducer hub 131 and the lower portion 110 of the septum 197 allows for the septum to be centered on the base 121.

The exemplary embodiment described above can be adapted for use with either intradermal or subcutaneous injections. In addition, a different method of maintaining the fluid connection is possible other than through the penetrating member 199 and septum 197. For example, a coiled tube connected to the introducer hub 131 that extends during insertion of the introducer needle 134, and then recoils upon retraction of the introducer needle, can be used. Alternative methods may be used to insert the catheter and introducer needle. For example, an angled needle in contact with the skin and driven at a smaller angle can be used to enter the intradermal layer of the skin. Alternative methods of connecting the connector to the base can be used to facilitate connecting and disconnecting of the connector.

Although the exemplary embodiment described above is an infusion set, it will be apparent to those of ordinary skill in the art that the principles of the present invention are also applicable to patch pumps (self-contained infusion devices with integral reservoirs and pumping mechanisms) and other types of medical infusion and injection devices.

Second Exemplary Embodiment

Figure 9:
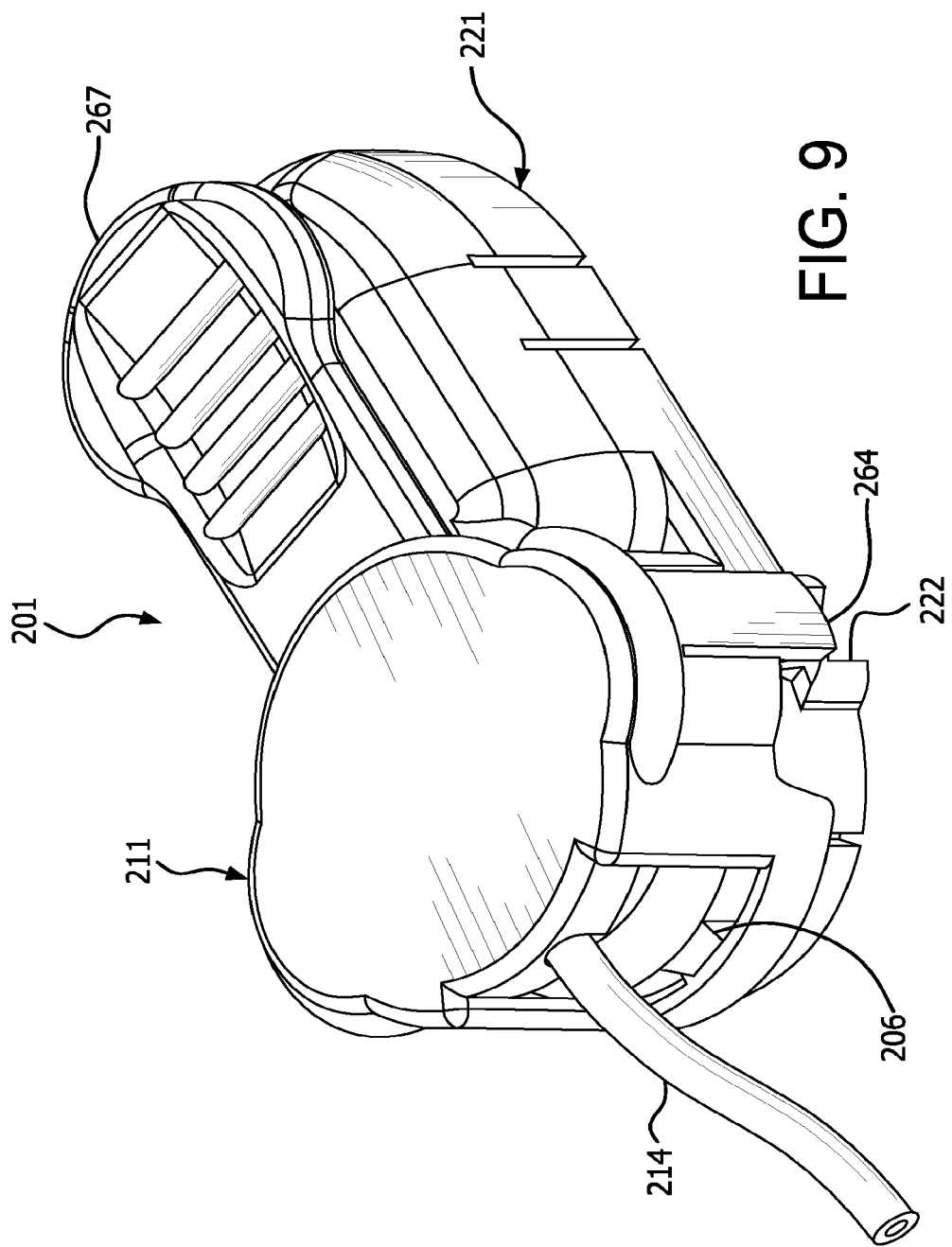
FIG. 9 is a perspective view of an infusion set according to a second exemplary embodiment of the present invention.

An infusion set 201 in accordance with a second exemplary embodiment of the present invention is shown in FIGS. 9-22. A base 221 of the infusion set 201, as shown in FIG. 9, is preferably provided with a skin-securing, adhesive layer 202 (FIG. 20) to secure the infusion set to the skin surface at a desired catheter insertion site. The adhesive layer ensures that the base 221 is at the proper position relative to the skin surface, and that the skin is secured during insertion to further aid introducer needle insertion with a reduced risk of tenting of the skin surface. The base has a first recess 222 and a second recess (not shown) adapted to receive tabs of a fluid connector 211, thereby securing the fluid connector 211 to the base 221 to fully assemble the infusion set 201, as shown in FIG. 9. A first ramped surface 225 (FIG. 20) slopes downwardly and outwardly toward the first recess 222, thereby facilitating the fluid connector tab to slide down into the first recess and creating a snap fit connection. A second ramped surface 226 (FIG. 20) slopes outwardly at an end of the first recess 222, thereby allowing the fluid connector 211 to be rotated with respect to the base 221 to allow the connector tabs to be released from the base recesses 222 to disconnect the fluid connector 211 from the base 221, as shown in FIG. 20.

Figure 10:
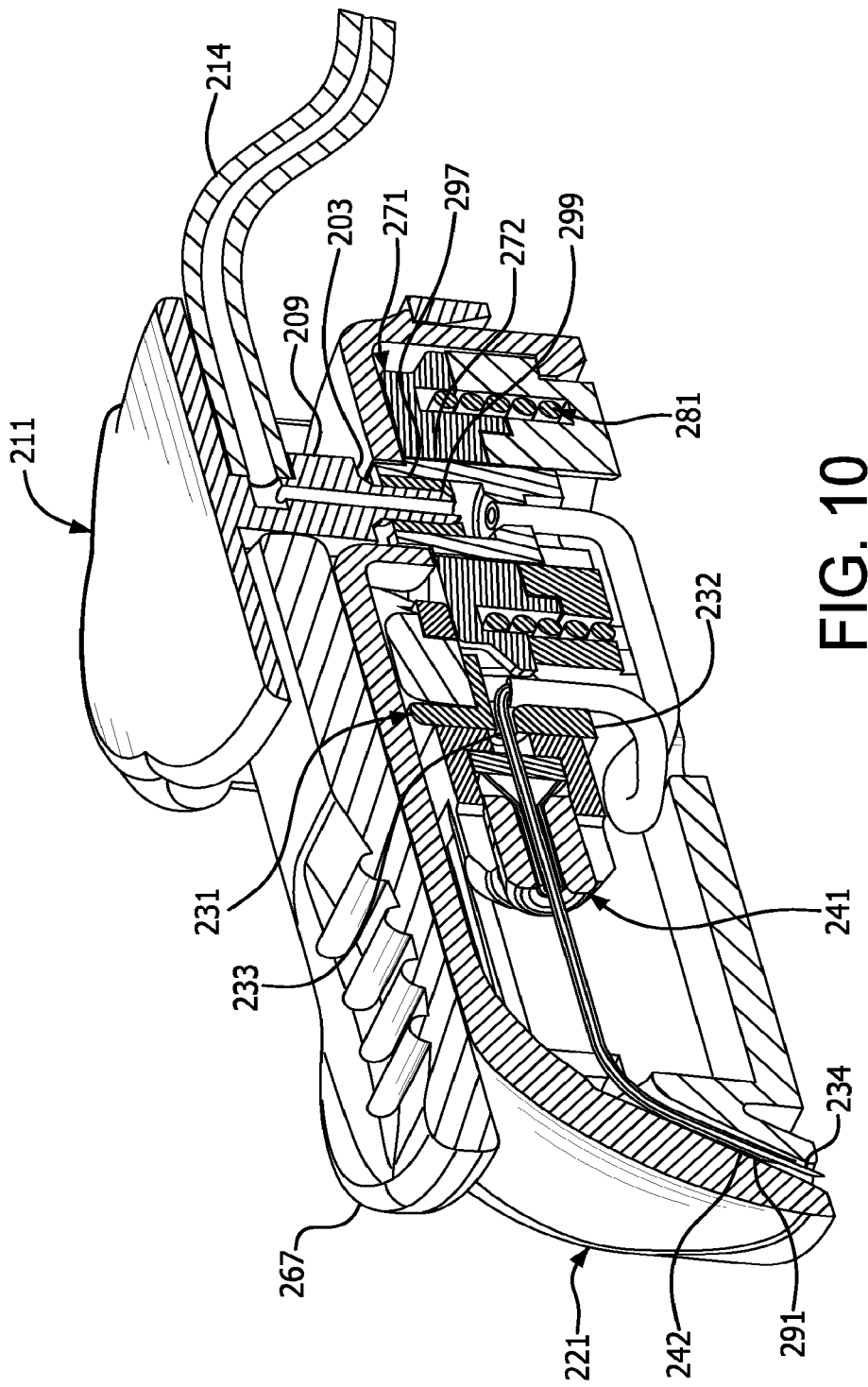
FIG. 10 is a perspective view in cross-section of the infusion set of FIG. 9.
Figure 12:
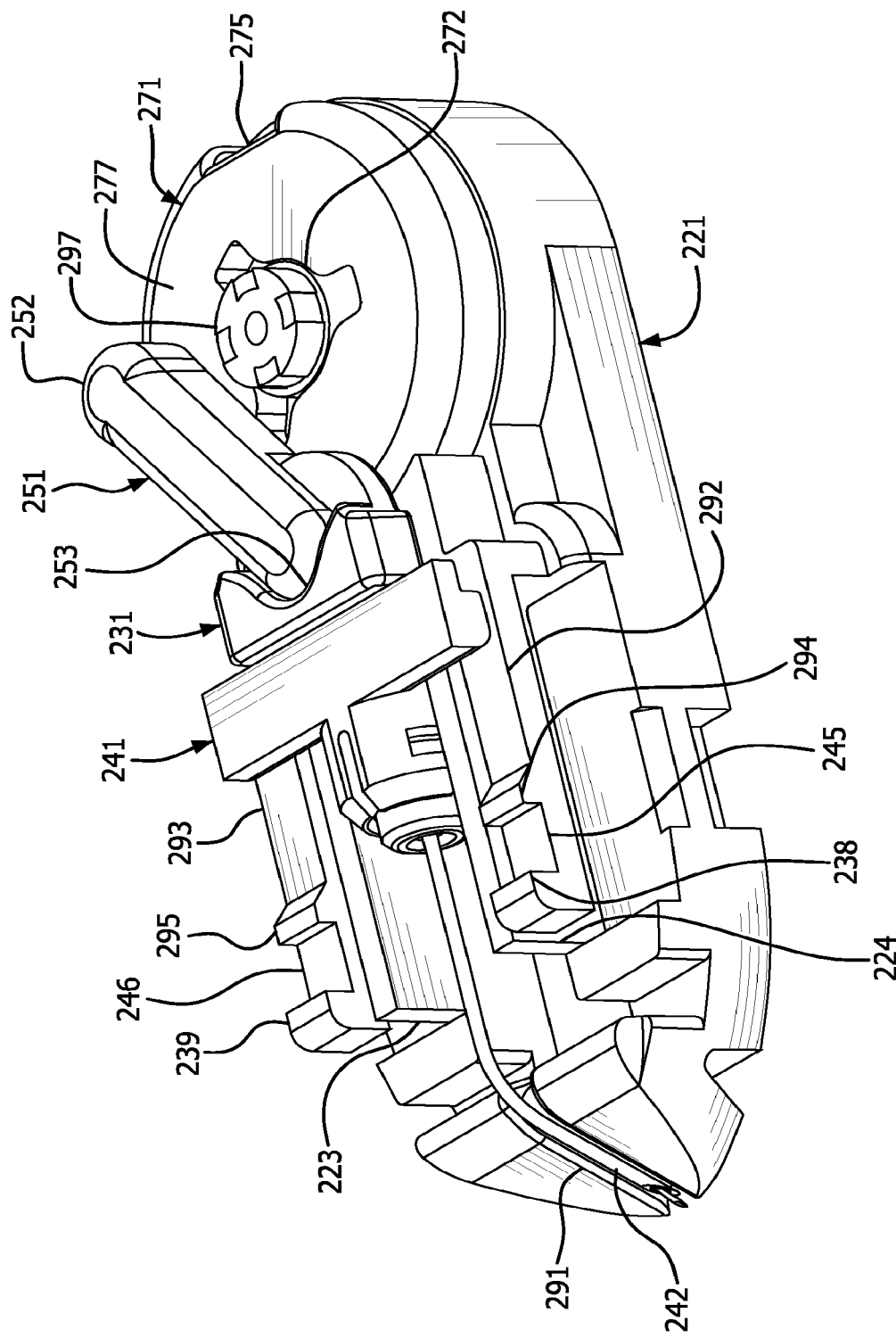
FIG. 12 is a partial perspective view of the infusion set of FIG. 9 with the catheter and introducer hubs in first positions.

An introducer hub 231 is movably disposed in the base 221 of the infusion set 201, as shown in FIG. 12. The introducer hub 231 has an opening 233 to receive an introducer needle 234, as shown in FIGS. 10 and 15. A lower portion 232 of the introducer hub 231 is disposed between guide rails 223 and 224 of the base 221, as shown in FIG. 12, to guide linear movement of the introducer hub 231. The introducer hub 231 is movable from a first position shown in FIG. 12, to a second position shown in FIG. 14, and back to the first position shown in FIG. 16. When the introducer hub 231 is in the first position, the introducer needle 234 is disposed within the base 221, thereby preventing any accidental introducer needle sticks. When the introducer hub 231 is in the second position, the introducer needle 234 is exposed outside of the base 221 such that a patient's skin can be pierced to insert an angled catheter 242.

Figure 13:
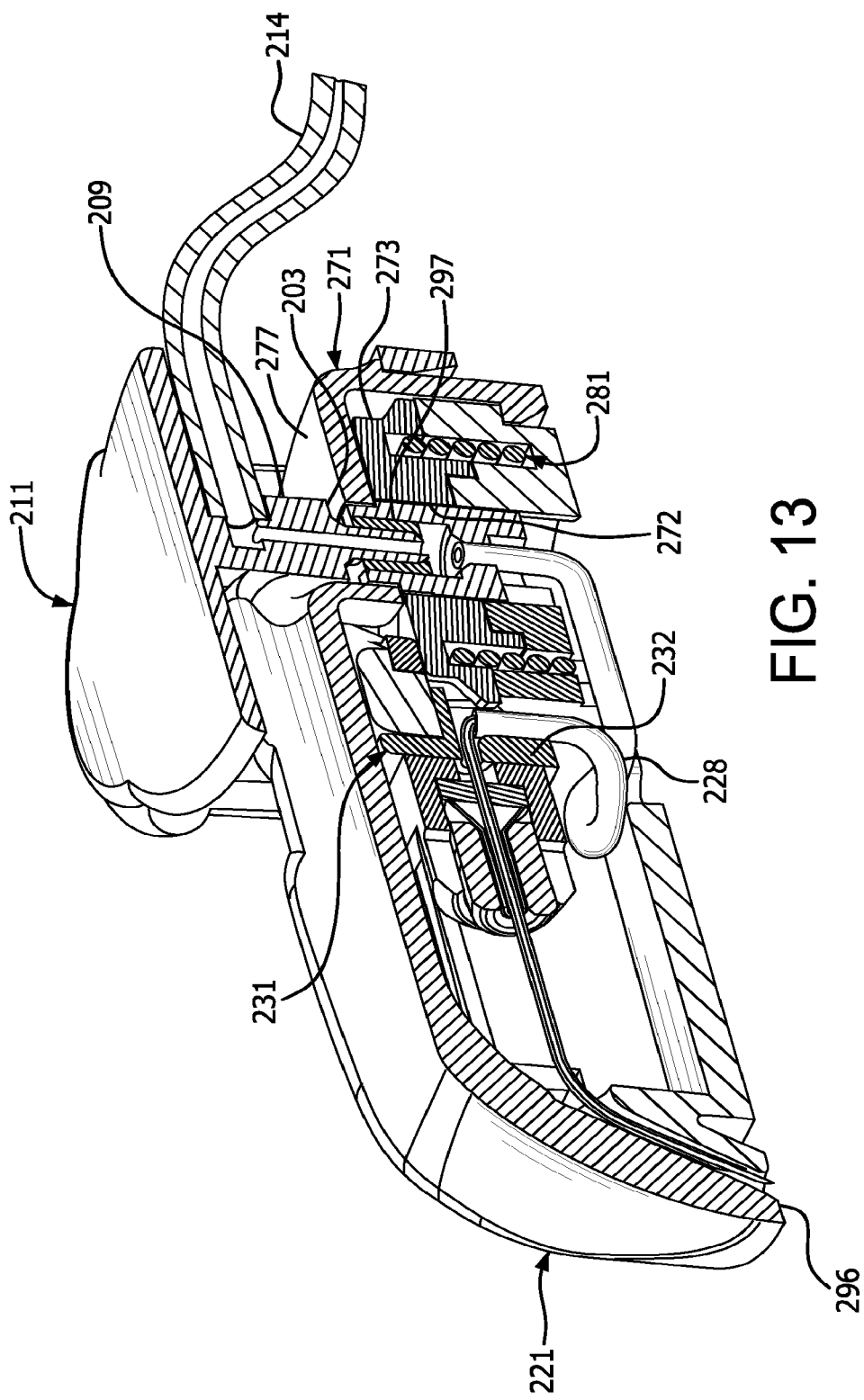
FIG. 13 is a perspective view in cross-section of the infusion set of FIG. 12.

A catheter hub 241 abuts the introducer hub 231, as shown in FIGS. 12-15. The flexible catheter 242 is rigidly connected to the catheter hub 241. The introducer needle 234 is movably disposed within the catheter 242, as shown in FIGS. 10 and 15. Linear movement of the introducer hub 231 results in linear movement of the catheter hub 241 because of the engagement of the introducer hub 231 with the catheter hub 241. The catheter hub 241 is movable between a first position shown in FIG. 12, and a second position shown in FIG. 14. When the catheter hub 241 is in the first position, the catheter 242 is disposed within the base 221, as shown in FIG. 13. When the catheter hub 241 is moved to the second position, the catheter 242 is moved out of the base 221, as shown in FIG. 15, and is insertable at an angle under the surface of a patient's skin.

Figure 14:
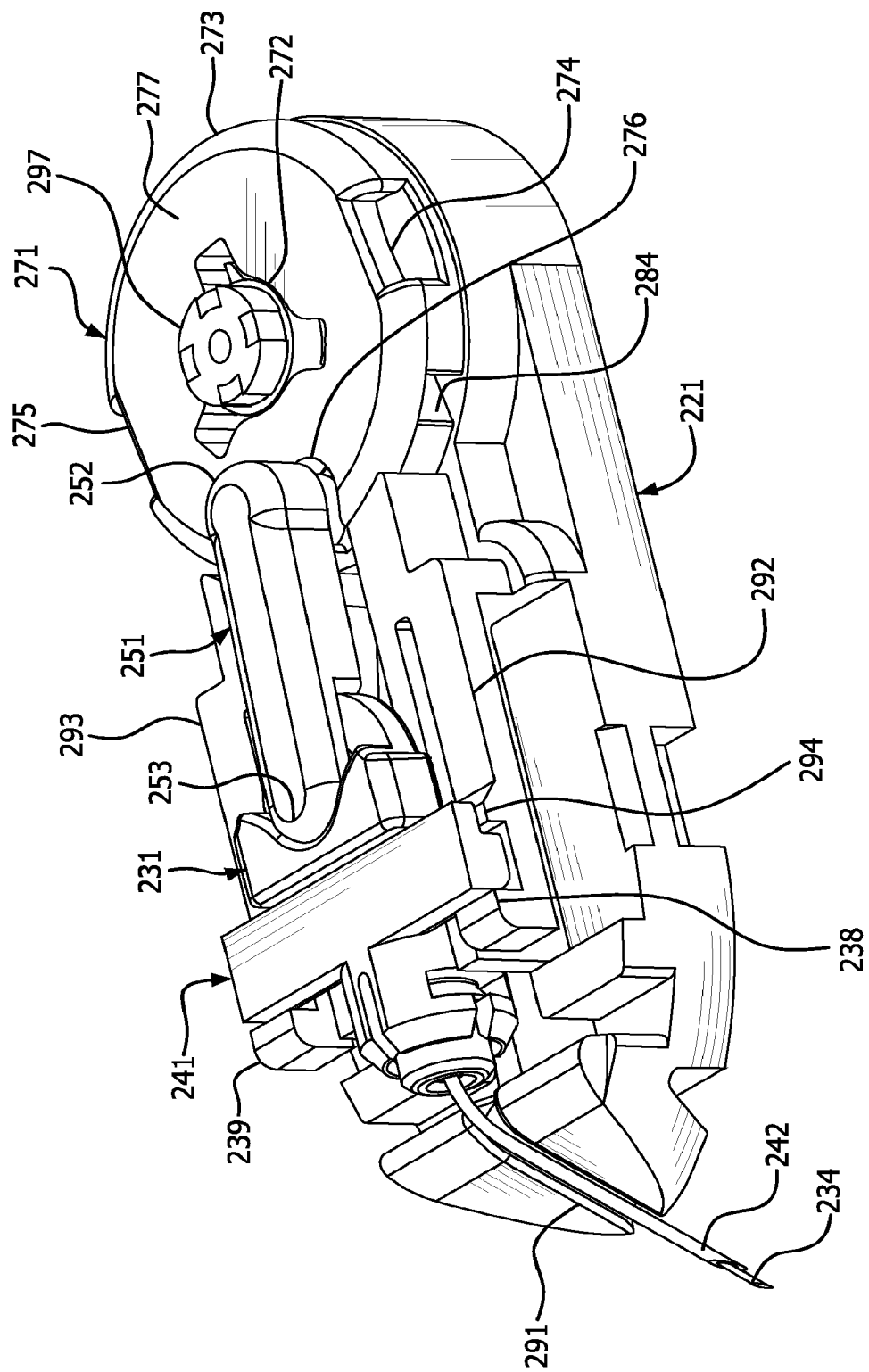
FIG. 14 is a partial perspective view of the infusion set of FIG. 9 with the catheter and introducer hubs in second positions.
Figure 15:
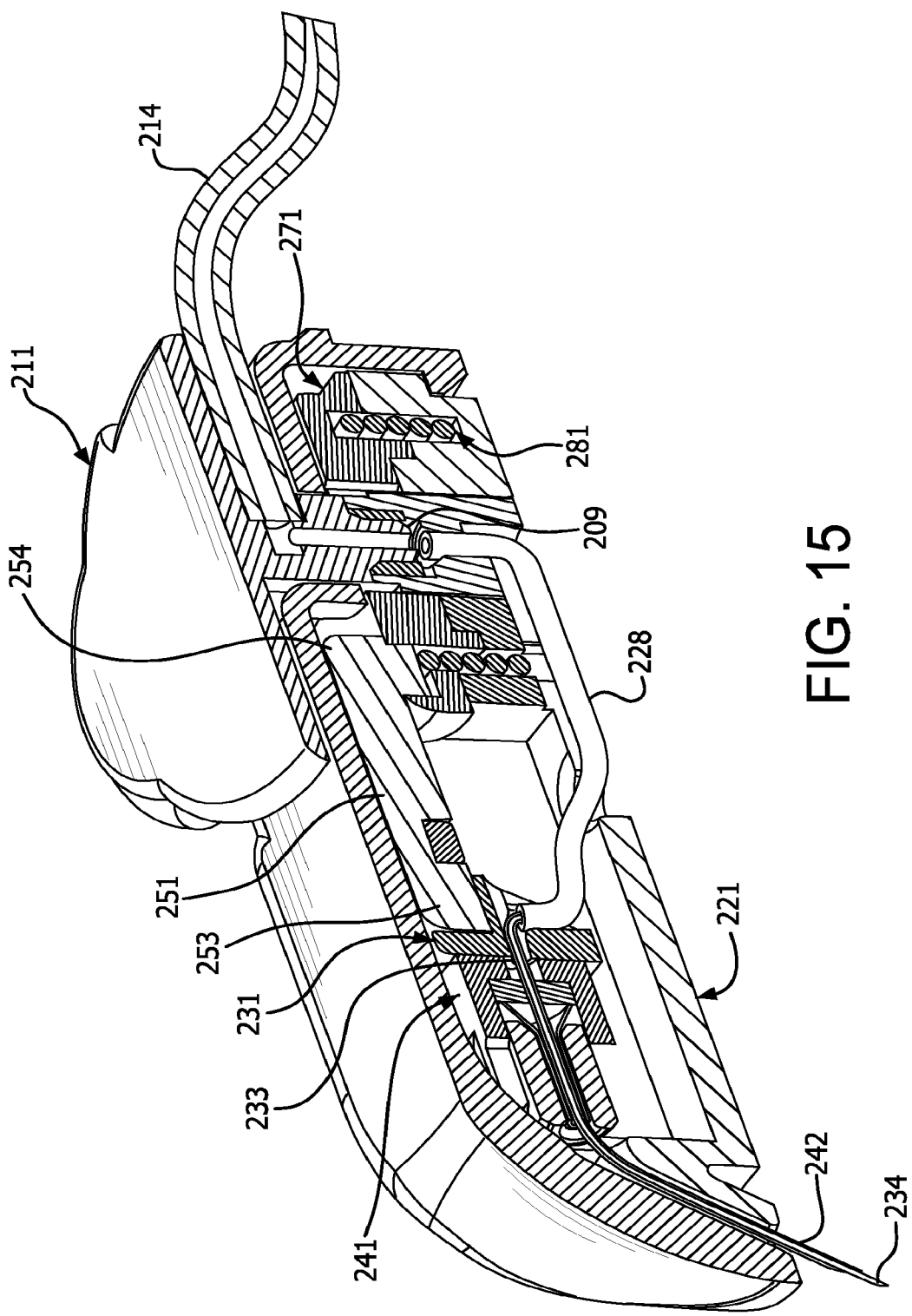
FIG. 15 is a perspective view in cross-section of the infusion set of FIG. 14.

A disc 271 is rotatably disposed in the base 221, as shown in FIGS. 10 and 12-18. The disc 271 has an inner perimeter 272 forming an aperture therethrough and an outer perimeter 273, as shown in FIGS. 10, 12 and 14. A torsion spring 281 is connected to the disc 271. Preferably, the torsion spring 281 is a 360 degree torsion spring, i.e., the torsion spring 281 causes the disc 271 to rotate 360 degrees upon release. First and second recesses 274 and 275 are formed in the outer perimeter 273 of the disc 271, as shown in FIG. 14. An opening 276 is formed in an upper surface 277 of the disc, as shown in FIG. 14 and receives a first end 252 of a linking arm 251.

Figure 21:
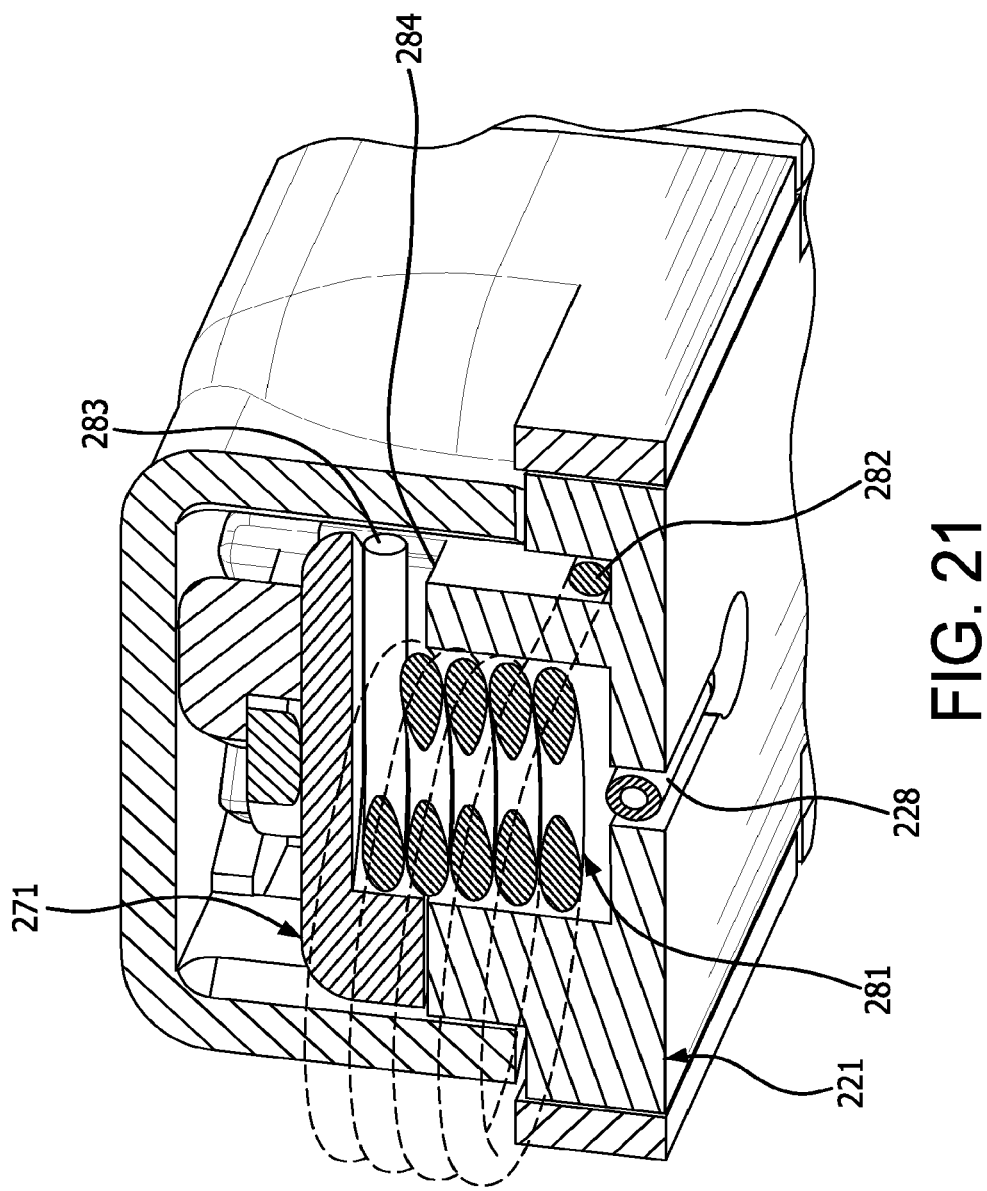
FIG. 21 is a perspective view in cross-section of the base of the infusion set showing first and second ends of a torsion spring.

The torsion spring 281 has a first end 282 rigidly fixed to the base 221, as shown in FIG. 21. A second end 283 of the torsion spring 281 is fixed to the disc 271, as shown in FIGS. 14 and 21. An opening 284 can be formed in the disc 271 to receive the second end 283 of the torsion spring 281.

The linking arm 251 connects the disc 271 to the introducer hub 231, thereby converting rotational movement of the disc 271 into linear movement of the introducer hub 231. The first end 252 of the linking arm 251 is connected to the disc 271, as shown in FIGS. 12 and 14-16. A second end 253 of the linking arm 251 is connected to the introducer hub 231.

Figure 17:
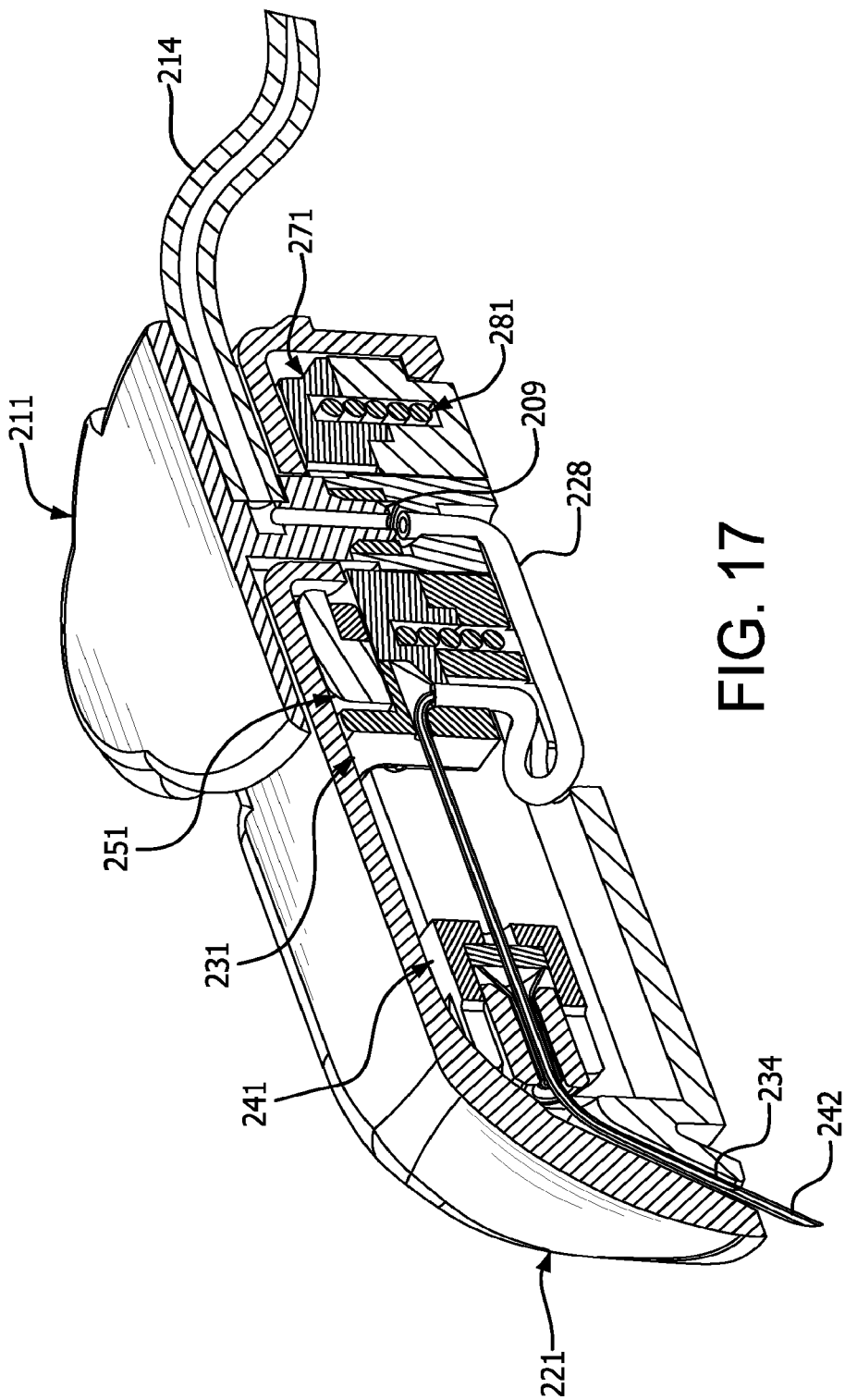
FIG. 17 is a perspective view in cross-section of the infusion set of FIG. 16.
Figure 18:
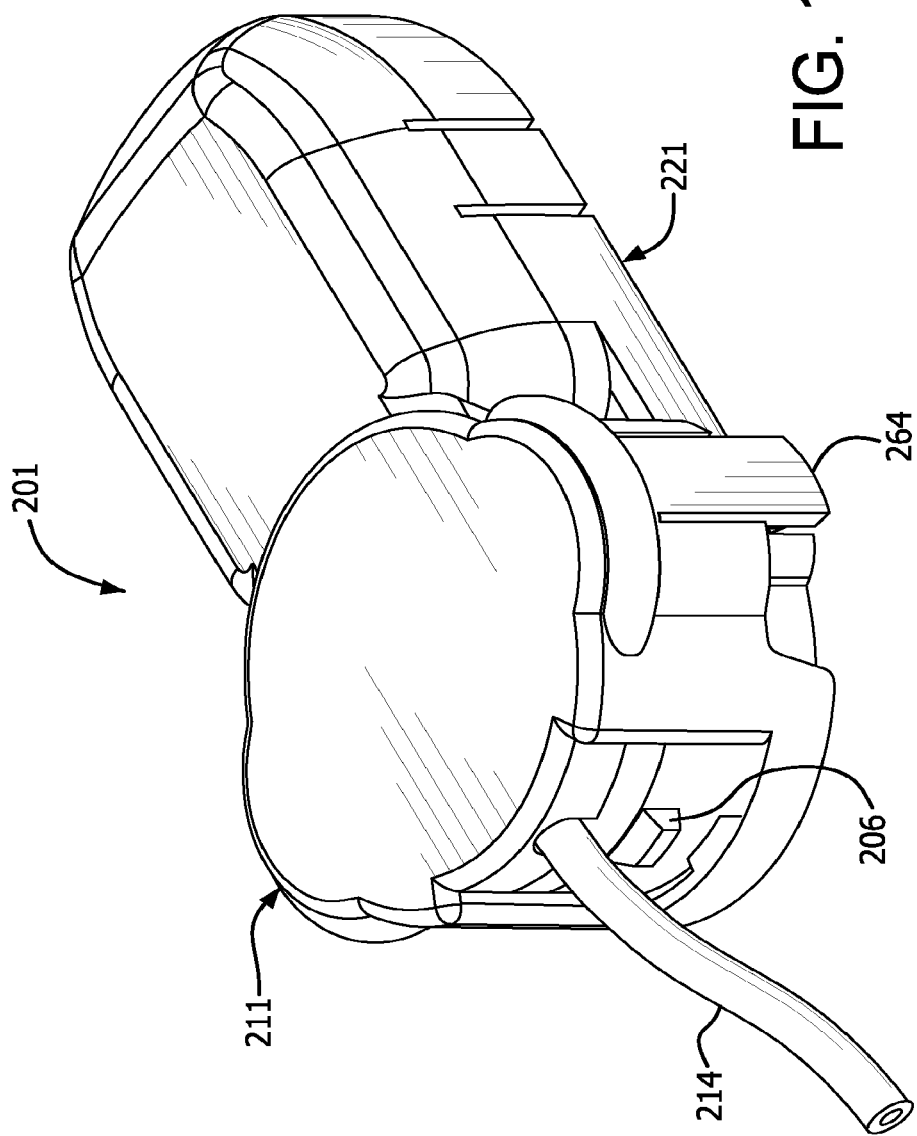
FIG. 18 is a perspective view of the infusion set of FIG. 9 with a connector moved to a second position.
Figure 22:
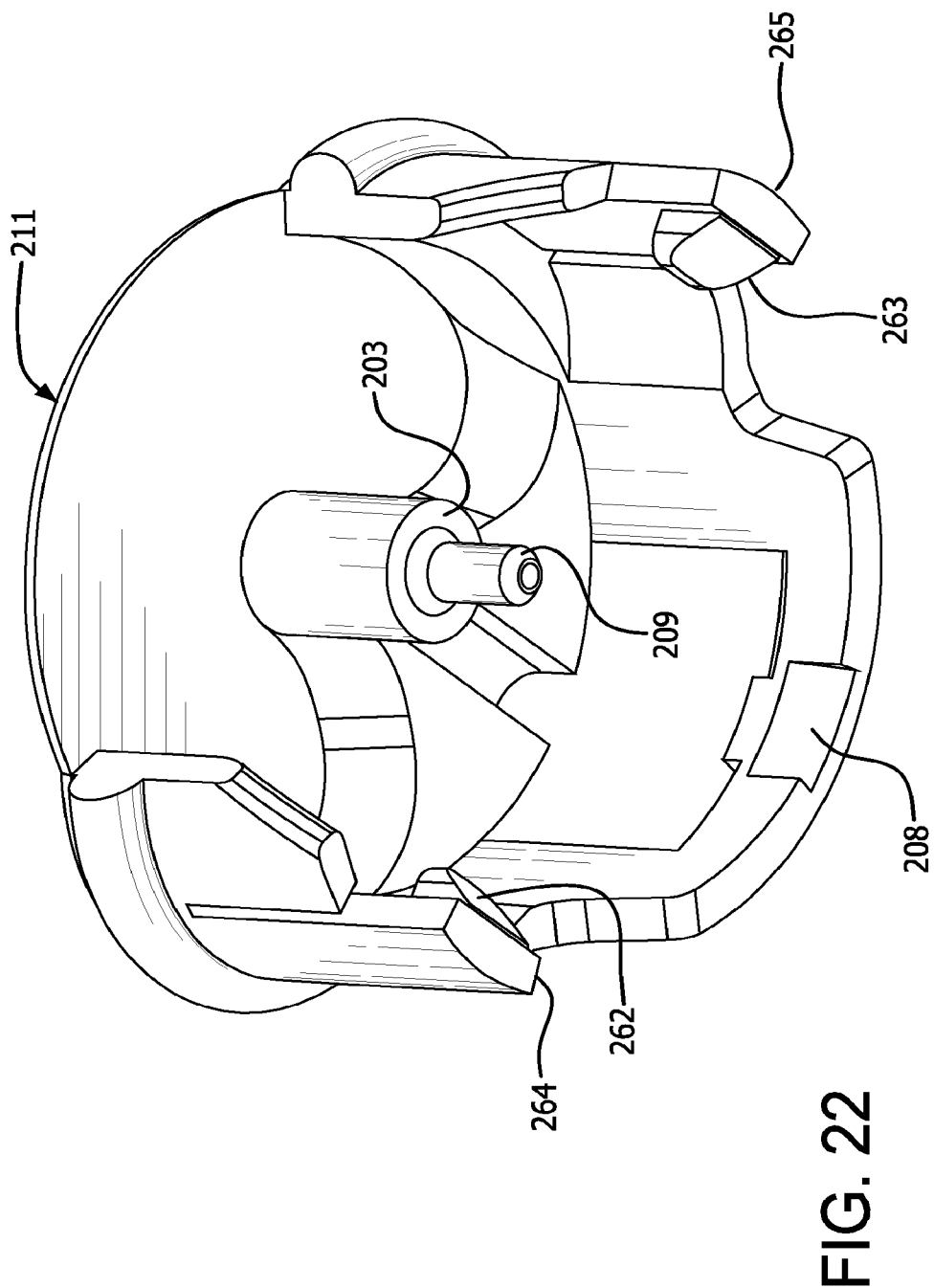
FIG. 22 is a lower perspective view of the connector.

The fluid connector 211 is movable between a first, or up, position as shown in FIGS. 9, 10 and 13, and a second, or down, position as shown in FIGS. 15 and 17. The fluid connector 211 is removably connected to the base 221 such that the fluid connector 211 can be removed after the catheter 234 has been inserted, as shown in FIG. 20. Tabs 262 and 263 extend inwardly from free ends of arms 264 and 265 extending downwardly from an upper surface 266 of the connector 211, as shown in FIGS. 20 and 22. When the connector 211 is in the first position, as shown in FIGS. 9, 10 and 13, tabs extending downwardly from first and second locking ears 205 and 207 (FIG. 20) are received within the recesses 274 and 275 of the disc 271, thereby preventing rotational movement of the disc 271. When the connector 271 is pressed downwardly to the second position, as shown in FIGS. 15 and 17, a shoulder 203 (FIG. 22) of a downwardly extending post 209 of the connector engages the upper surface of the septum assembly 297, thereby pushing the septum assembly 297 downwardly and disengaging the locking tabs on the septum assembly 297 from recesses in the inner perimeter 272 of the disc 271. When the tabs of the septum assembly 297 are not received by the recesses in the inner perimeter of the disc 271, the disc 271 can rotate due to the torque applied by the torsion spring 281.

Arms 264 and 265 extend downwardly from the connector 211, as shown in FIGS. 20 and 22. Tabs 262 and 263 disposed at the free ends of the arms 264 and 265 are received on the ramps 225 of the base 221, thereby maintaining the connector 211 in the up position shown in FIG. 9. When the catheter 242 is to be inserted, a locking member 267 is removed such that the fluid connector 211 can be pushed downwardly to the second position. The downward movement of the fluid connector 211 flexes the arms 264 and 265 outwardly such that the arms 264 and 265 slide down the ramps 225 into the recesses 222 in the base 221. The snap connection between the connector arms 264 and 265 and the recesses 222 in the base 221 retains the fluid connector 221 connected to the base 221 after inserting the catheter 242.

Figure 16:
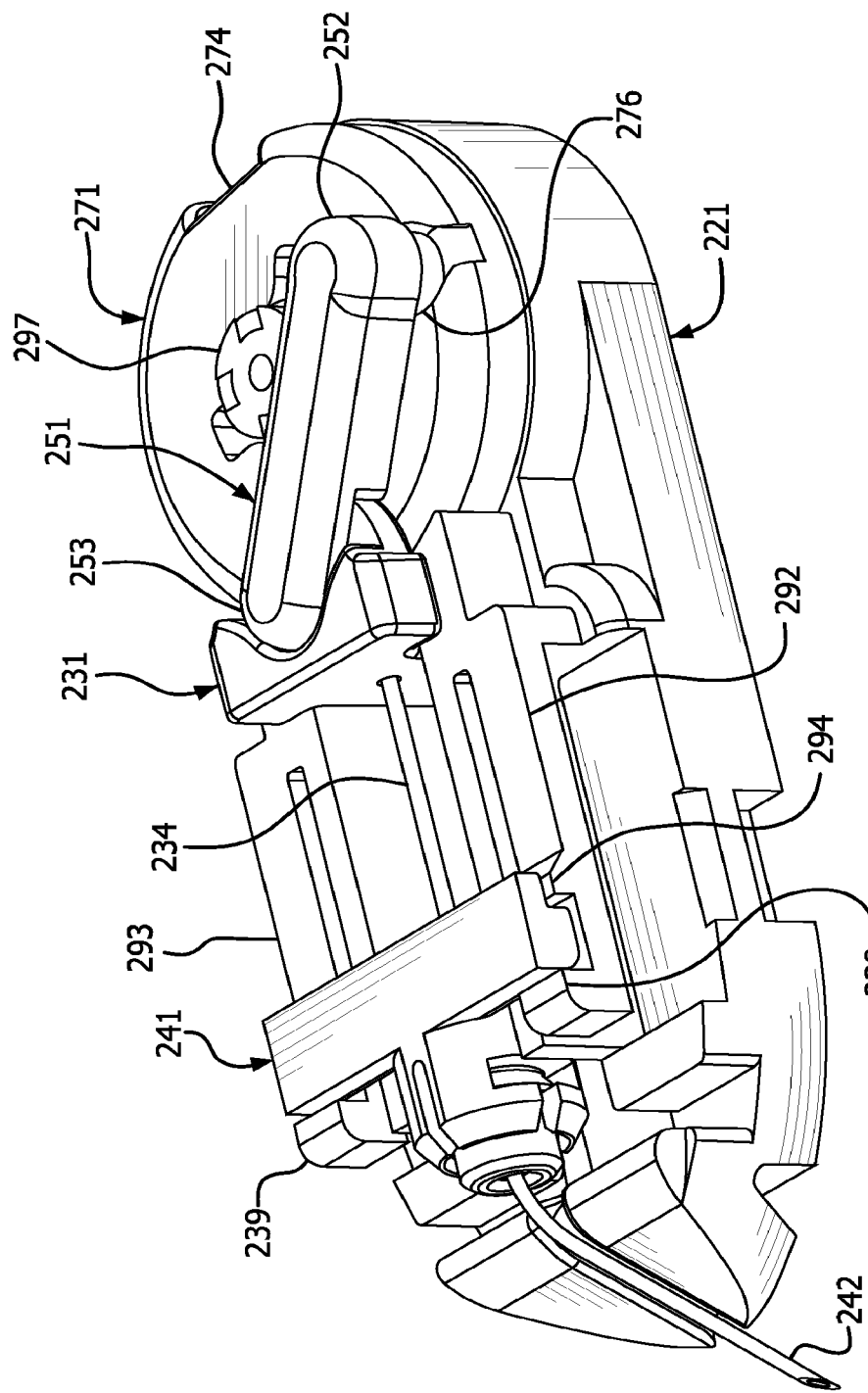
FIG. 16 is a partial perspective view of the infusion set of FIG. 9 with the catheter hub in the second position and the introducer hub returned to the first position.

An angled guide 291 is provided in the base 221 to guide movement of the introducer needle 234 and the catheter 242, as shown in FIGS. 10 and 12. The angled guide 291 creates an angle with respect to the surface of the skin of between approximately 30 and 45 degrees, inclusive, and preferably about 45 degrees. An opening 296 is formed in the base 221 at the end of the angled guide 291 to allow the introducer needle 234 and catheter 242 to exit the base 221. First and second flexible arms 292 and 293 extend in the base 221 in the direction of movement of the catheter hub 241, as shown in FIGS. 12, 14 and 16. Upwardly extending hooks 294 and 295 are disposed proximate an end of each of the flexible arms 292 and 293. Stop members 238 and 239 are disposed at the ends of each of the flexible arms 292 and 293, as shown in FIG. 12. Recesses 245 and 246 are formed on each flexible arm 292 and 293 between the hooks 294 and 295 and the stop members 238 and 239, respectively, to receive the catheter hub 241 in the second position.

A septum 297 is disposed in the aperture formed in the disc 271, as shown in FIG. 12. Preferably, the septum 297 has a slit to facilitate receiving a penetrating member, or sharp, of the fluid connector 211, as shown in FIG. 15, although the slit may not be required in some cases.

Figure 11:
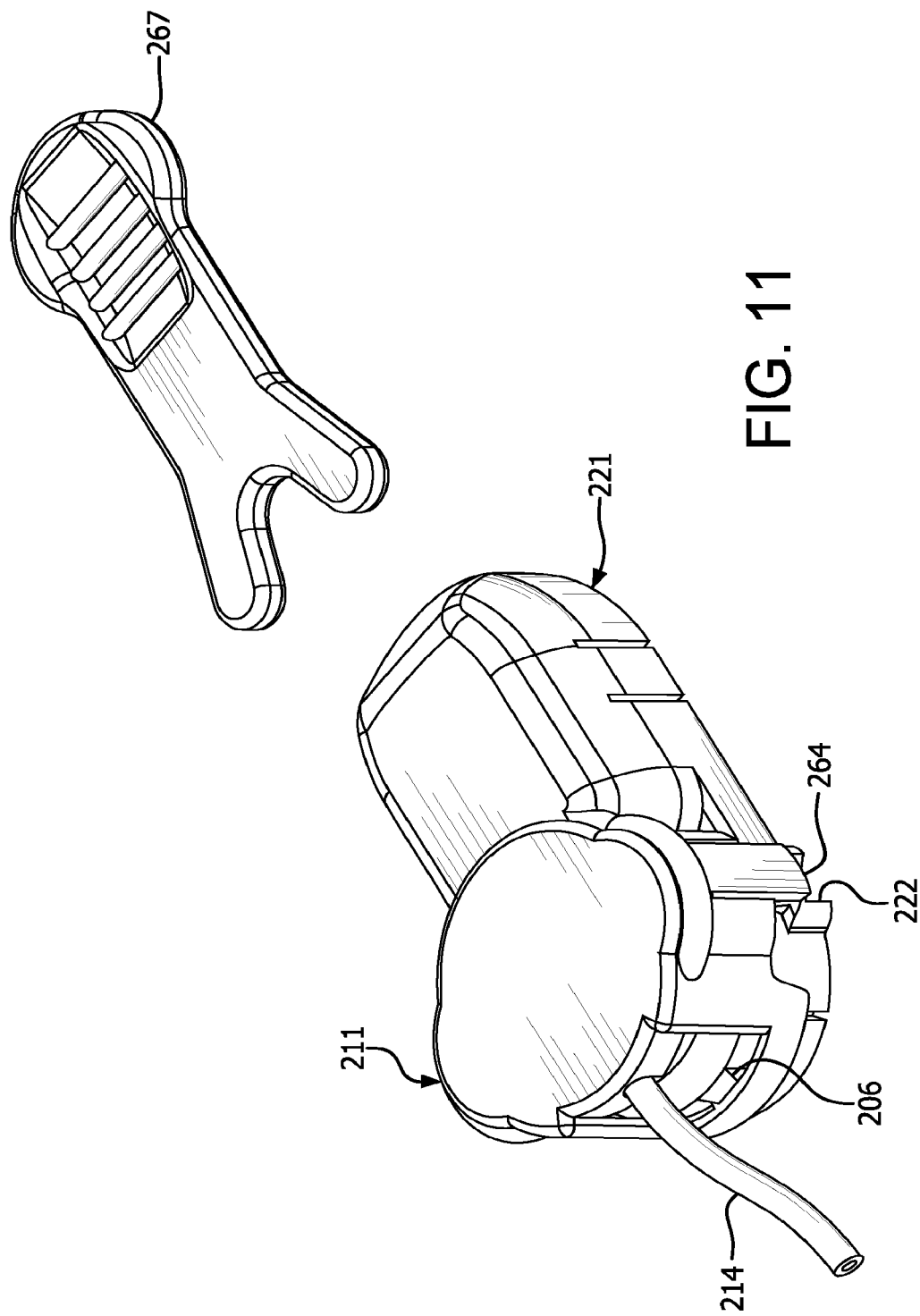
FIG. 11 is a perspective view of the infusion set of FIG. 9 with a locking member removed.

The fluid connector 211 has first and second flexible arms 264 and 265, as shown in FIGS. 9, 11 and 22, that engage the first and second recesses 222 in the base 221 to secure the fluid connector 211 to the base 221. Tubing 214 extends from the connector 211 and is adapted to connect to a pump (not shown). The tubing 214 is connected to a penetrating member extending downwardly from the post 209 of the connector 211, and a fluid path is formed therebetween. The penetrating member 299 is adapted to penetrate the septum 297 when the connector 211 is connected to the base 221, as shown in FIGS. 10 and 15.

FIG. 9 is a perspective view of the infusion set 201 ready to be inserted by a user. A tab 206 on the base 221 is received by a recess 208 in the fluid connector, as shown in FIGS. 9 and 22, to prevent accidental removal of the fluid connector 211 from the base 221 prior to an insertion procedure. The locking member 267 is disposed between the base 221 and the connector 211 to prevent accidentally activating the torsion spring 281 and exposing the needle 234 and catheter 242 prior to a desired insertion procedure.

The fluid connector 211 is in the up, or first, position, as shown in FIG. 9. In this position, the locking tabs of the septum assembly 297 are disposed in the recesses in the inner perimeter 272 of the disc 271, thereby preventing rotation of the disc 271. The catheter hub 241 and the introducer hub 231 are disposed to the right of the base 221 spaced from the hooks 294 and 295 of the base flexible arms 292 and 293, as shown in FIG. 12. The catheter 242 and the introducer needle 234 are disposed within the base 221, thereby substantially preventing accidental introducer needle sticks.

An adhesive backing (not shown) is removed from the base 221 to expose an adhesive layer 202 (FIG. 20) on a lower surface of the base, such that the base can be firmly secured to a desired location on the skin. To insert the catheter 242, the locking member 267 is removed as shown in FIG. 11 such that the fluid connector 211 can be pushed downwardly to a second, or down, position to release the torsion spring 281, thereby driving rotational movement of the disc 271. The downward movement of the connector 211 causes the shoulder 203 of the connector post 209 to engage the septum assembly 297 and push the septum assembly 297 downwardly, thereby moving the locking tabs of the septum assembly 297 out of engagement with recesses in the inner perimeter 272 of the disc 271, which frees the disc 271 to rotate. The connector arms 264 and 265 move from the ramp 225 to the recesses 222 in the base 221, thereby securing the fluid connector 211 to the base 221. The second end of the torsion spring 281 rotates with the disc 271 as the torsion spring 281 causes the disc 271 to rotate.

As the disc 271 begins to rotate counter-clockwise as shown in FIGS. 12, 14 and 16, the linking arm 251 moves with the disc 271. The movement of the linking arm 251, in turn, results in linear movement of the introducer hub 231.

The introducer hub 231 is limited to linear movement by the guide rails 223 and 224, as shown in FIG. 12. The linear movement of the introducer hub 231 pushes the catheter hub 241 from the first position shown in FIG. 12 to the second position shown in FIG. 14. The introducer hub 231 pushes the catheter hub 241 along the base flexible arms 292 and 293 such that the catheter hub 241 flexes the arms 292 and 293 downwardly to pass over the hooks 294 and 295. After the catheter hub 241 passes over the hooks 294 and 295, the hooks snap back up to prevent rearward movement of the catheter hub 241 back along the flexible arms 292 and 293. Stop members 238 and 239 disposed at ends of the arms 292 and 293 prevent further forward linear movement by the catheter hub 241. Additionally, the forward linear movement of the catheter hub 241 and the introducer hub 231 results in forward movement of the catheter 242 and the introducer needle 234, respectively. The catheter 242 is fixedly attached to the catheter hub 241 and the introducer needle 234 is fixedly attached to the introducer hub 231. The angled guide 291 in the base guides the downwardly angled movement of the catheter 242 and introducer needle 234. The introducer needle 234 extends beyond the catheter 242 such that the introducer needle 234 pierces the surface of the skin to allow the catheter 242 to be inserted at an angle beneath the surface of the skin. The catheter hub 241 is securely received between the hooks 294 and 295 and the stop members 238 and 239 to prevent rearward linear movement of the catheter hub 241 after the catheter 242 has been inserted. The disc 271 has rotated approximately 180 degrees at this point, as shown in FIG. 14.

As the disc 271 continues to rotate past the 180 degree point, the linking arm 251 causes the introducer hub 231 to move linearly rearwardly between the guide rails 223 and 224. The hooks 294 and 295 of the base flexible arms 292 and 293 prevent rearward movement of the catheter hub 241. The rearward linear movement of the introducer hub 231 pulls the introducer needle 234 out of the insertion site, leaving the catheter 242 inserted at an angle beneath the surface of the skin, as shown in FIG. 16. As the disc 271 continues to rotate, the introducer needle 234 is withdrawn entirely into the base 221 of the infusion set 201. The torsion spring 281 can be pre-loaded such that the disc 271 does not rotate more than approximately 360 degrees. Additionally, a stop tab (not shown) can be disposed in the base that mates with a corresponding stop tab (not shown) on the disc 271 to prevent the disc from rotating more than approximately 360 degrees. The infusion set 201 is now ready to begin infusing insulin.

A fluid path is created from the connector tubing 214, through the septum 297, through the post 209, through the base tubing 228 fluidly connecting the septum 297 and the introducer hub 231, through the introducer needle 234 and into the catheter 242, as shown in FIG. 17. The base tubing 228 is flexible such that the base tubing 228 moves with the introducer hub 231 between first and second positions, as shown in FIGS. 12, 14 and 16.

Figure 19:
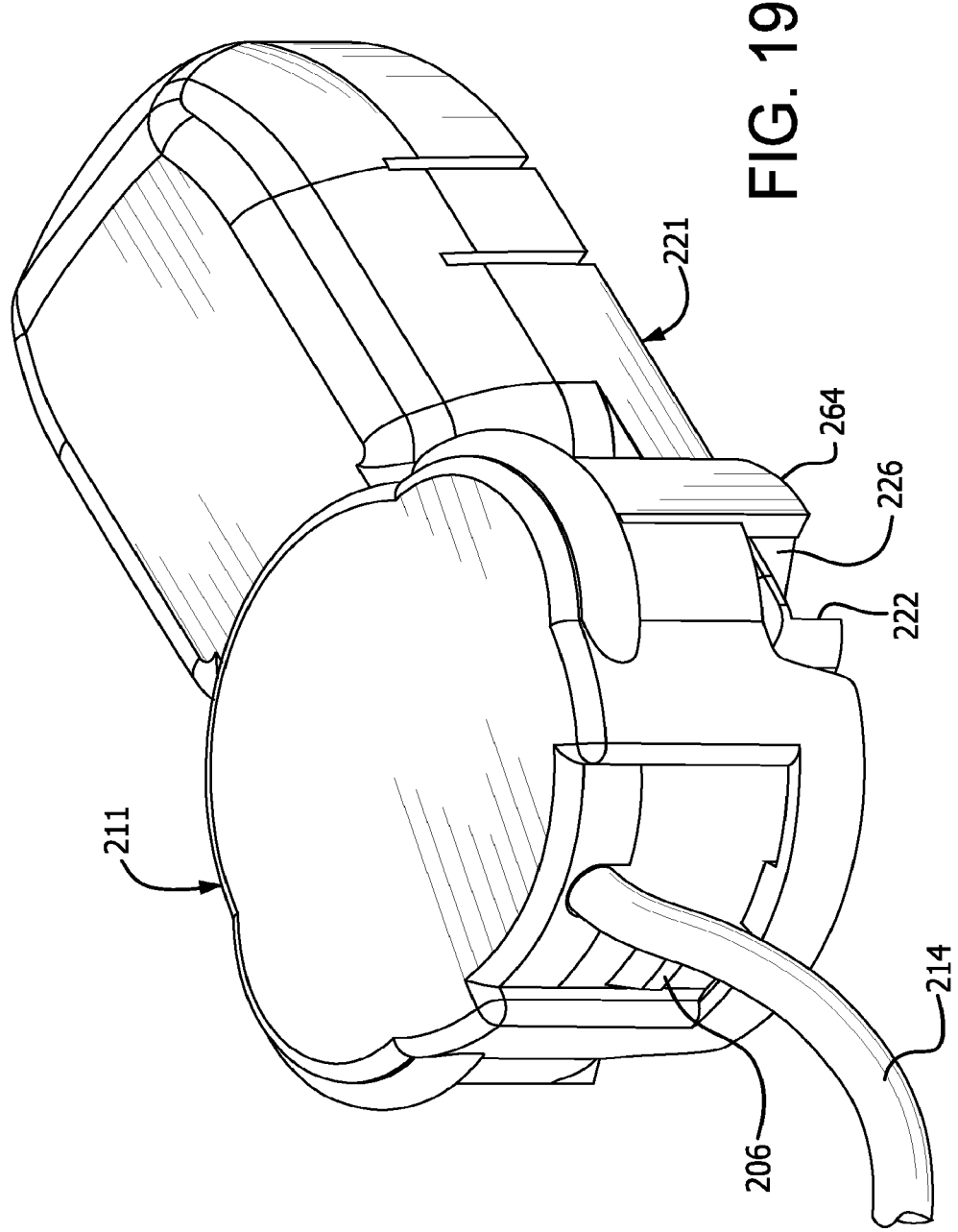
FIG. 19 is a perspective view of the infusion set of FIG. 18 with the connector rotated prior to removal thereof.
Figure 20:
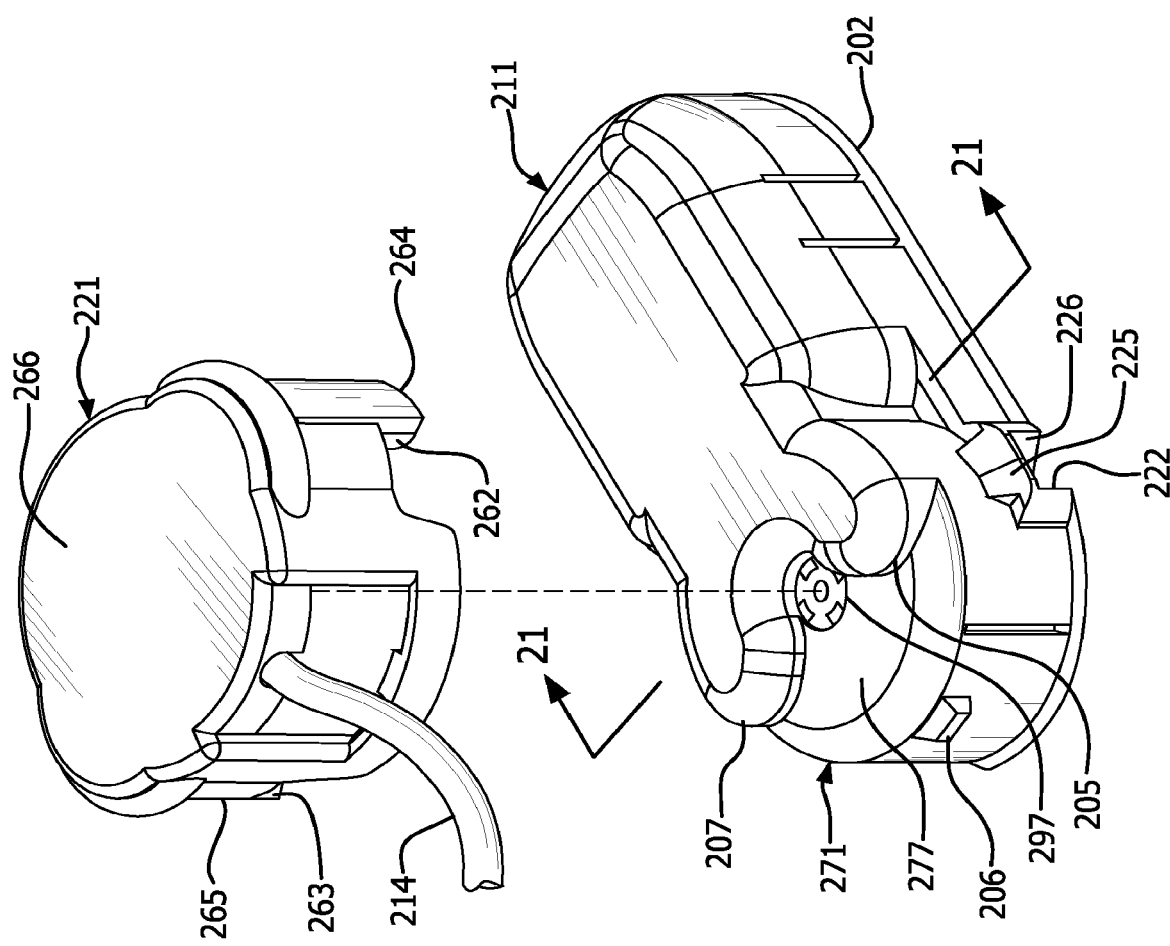
FIG. 20 is a perspective view of the infusion set of FIG. 19 with the connector removed from a base of the infusion set.

The connector 211 and tubing 214 can be easily removed by rotating the connector 211 relative to the base 221, as shown in FIGS. 19 and 20. The hooks of the connector arms 264 and 265 slide along the ramped surfaces 226 of the base recesses 222 causing the arms 264 and 265 to flex outwardly, thereby allowing the connector 211 to be easily disconnected from the base 221. The connector 211 can then be reconnected when desired as described above.

The pre-loaded torsion spring 281, when released by the connector 211, performs both the insertion and retraction of the introducer needle 234. Torsion springs can store a large amount of energy within a small and flat profile. This is facilitated by the 360 degree rotation of the disc 271 driven by the torsion spring 281. The first 180 degree rotation of the disc 271 inserts the introducer needle 234, and the second 180 degree rotation of the disc retracts the introducer needle completely into the base 221. The torsion spring 281 can be pre-loaded to not less than 180 degrees and up to approximately 360 degrees to perform the insertion and retraction of the introducer needle 234.

The linking arm 251 between the introducer hub 231 and the disc 271 produces a cyclical piston movement. By using a flexible or bending introducer needle 234 and an angled catheter 242, the infusion set 201 can have a low profile. The angled guide 291 in the base 221 guides the introducer needle 234 downwardly into the surface of the skin. Moreover, the only action required by the user is to press the connector 211 downwardly. The insertion of the introducer needle 234 and the catheter 242 and the retraction of the introducer needle occur automatically. Additionally, by only requiring the user to push the connector 211 downwardly, the infusion set 201 can be positioned and used in hard-to-reach and awkward body locations.

The exemplary embodiment described above can be adapted for use with either intradermal or subcutaneous injections. Alternative methods of connecting the fluid connector 211 to the base 221 can also be used to facilitate connecting and disconnecting of the fluid connector, such as a fluid connector connectable to a side of the base 221.

Although the exemplary embodiment described above is an infusion set, it will be apparent to those of ordinary skill in the art that the principles of the present invention are also applicable to patch pumps (self-contained infusion devices with integral reservoirs and pumping mechanisms) and other types of medical infusion and injection devices.

Third Exemplary Embodiment

In accordance with a third exemplary embodiment of the present invention shown in FIGS. 23-35, an infusion set 301 includes an integral catheter 342 and blood glucose sensing element 372. Suitable types of electromechanical sensing elements are disclosed in U.S. Pat. Nos. 5,390,671, 5,391,250, 5,482,473, and 5,586,553, which are hereby incorporated by reference in their entirety. A pre-loaded torsion spring 381 inserts the catheter 342 and the sensing element 372. By integrating the sensing element 372 with the infusion set 301, the amount of equipment required to be carried by a user is reduced, as well as reducing the number of procedures a user must perform. The torsion spring 381 substantially simultaneously drives the insertion of two sharps, i.e., a catheter introducer needle 334 and the sensing element 372. The sensing element 372 can be a glucose oxidase sensor, a glucose binding protein sensor, or any other suitable sensor, and can be used either to allow intermittent user readings of blood glucose levels, closed loop control of infusion pump operation based on measured blood glucose levels (i.e., continuous glucose monitoring), or both.

Figure 26:
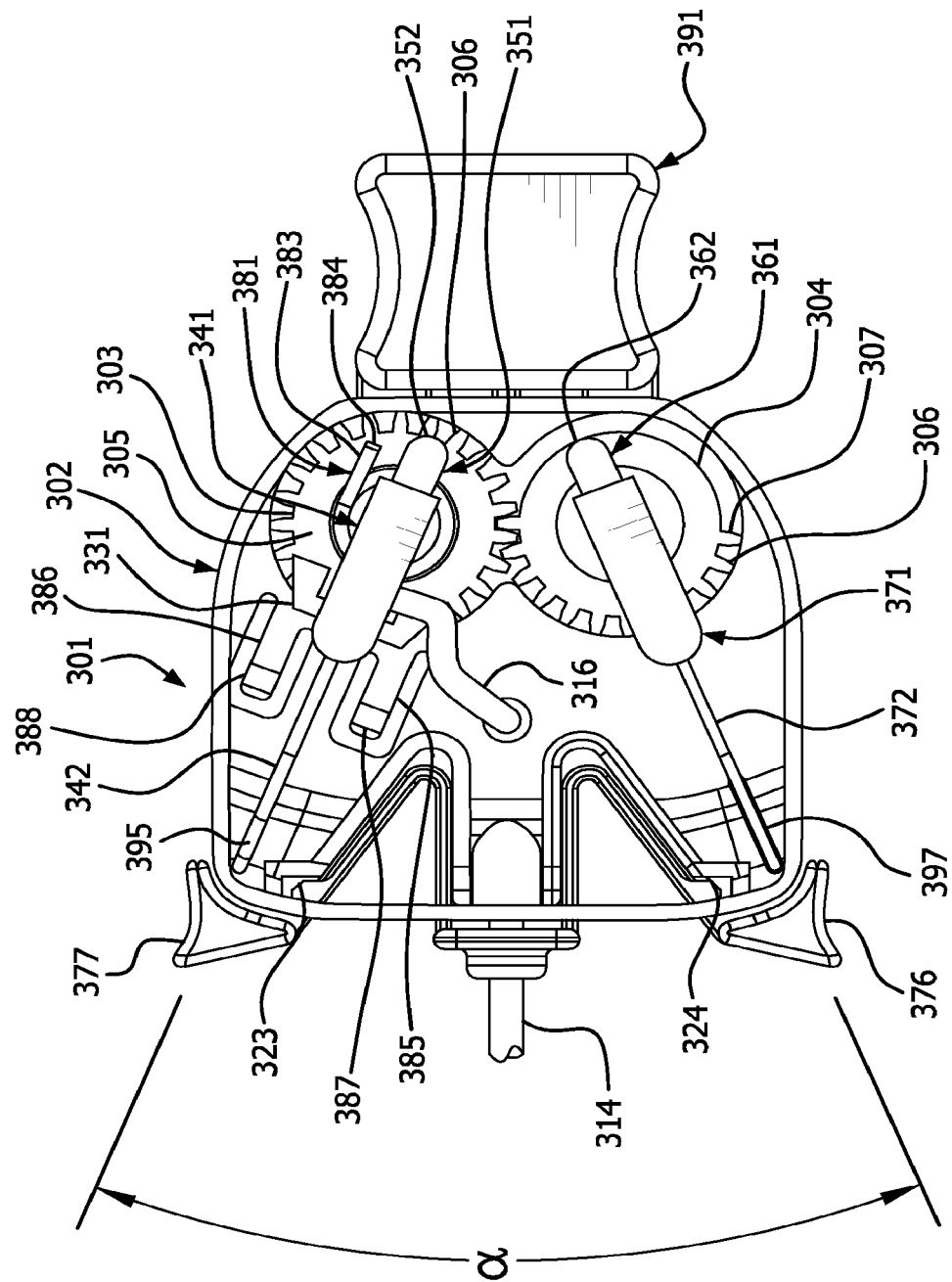
FIG. 26 is a partial top plan view of the infusion set of FIG. 23.

As shown in FIG. 26, the infusion set 301 has a housing or base 302 in which a drive gear 303 and a slave gear 304 are disposed. The drive gear 303 inserts and retracts the catheter introducer needle 334 and the catheter 342. The slave gear 304 inserts the sensing element 372. The catheter 342 and catheter introducer needle 334 are preferably flexible. The sensing element 372 is preferably a flexible sharps.

Figure 25:
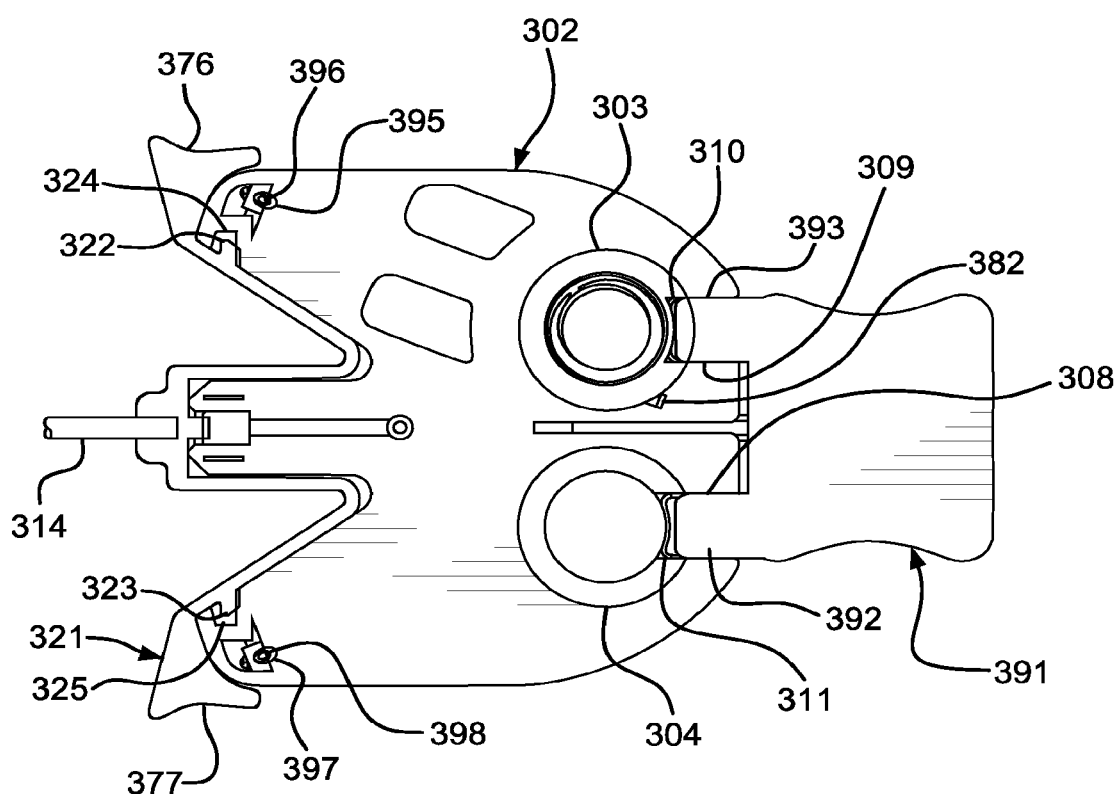
FIG. 25 is a bottom plan view of the infusion set of FIG. 23.

The drive gear 303 is connected to the torsion spring 381. A first end 382 of the torsion spring is connected to the housing 302 and a second end 383 of the torsion spring is connected to the drive gear 303, as shown in FIGS. 25 and 26. Preferably, a recess 384 in an upper surface 305 of the drive gear 303 receives the second end 383 of the torsion spring 381. A plurality of teeth 306 extend outwardly from an outer perimeter of the drive gear 303. Preferably, the plurality of teeth 306 extend continuously around the entire outer perimeter of the drive gear 303.

Figure 30:
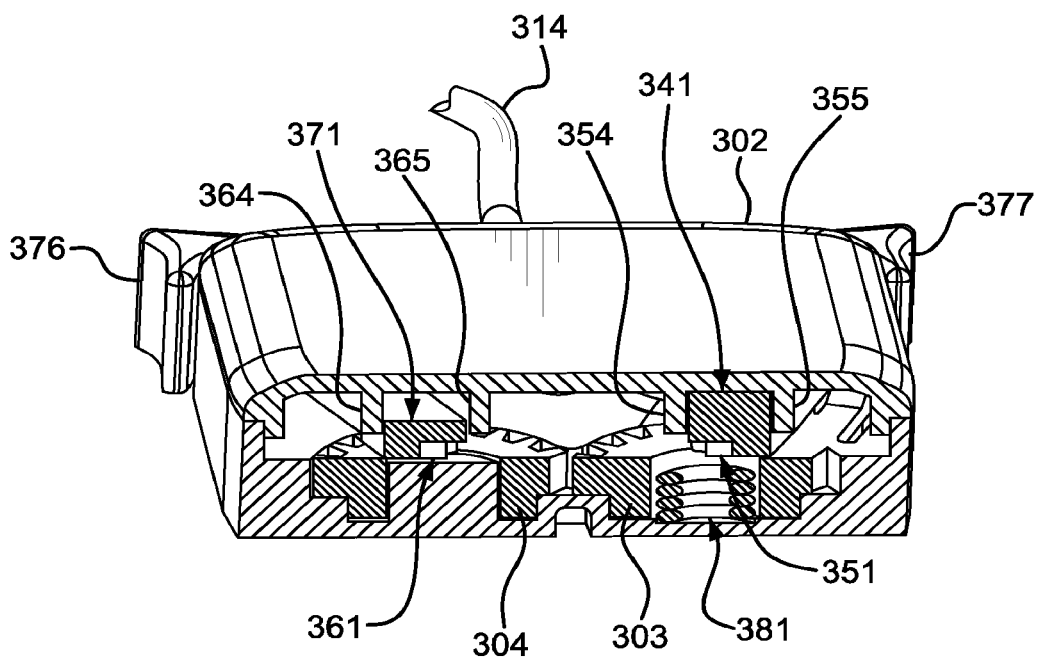
FIG. 30 is a partial perspective view in cross-section of the infusion set of FIG. 23 showing a drive and slave gear arrangement.

The slave gear 304 is disposed adjacent the drive gear 303 in the housing 302 such that teeth 307 of the slave gear 304 engage the drive gear teeth 306, as shown in FIGS. 26 and 30. Preferably, the slave gear teeth 307 extend continuously on a portion of an outer perimeter of the slave gear 304. Preferably, the slave gear teeth 307 extend approximately 180 degrees around the outer perimeter of the slave gear 304.

A catheter linking arm 351 has a first end 352 connected to the drive gear 303 and a second end 353 connected to a catheter introducer hub 341, as shown in FIGS. 26-29. Guide rails 354 and 355 in the housing 302 facilitate linear movement of the catheter introducer hub 341, as shown in FIG. 30.

A sensing element linking arm 361 has a first end 362 connected to the slave gear 304 and a second end connected to a sensing element hub 371, as shown in FIG. 26. The sensing element linking arm 361 is connected to the slave gear 304 in a substantially similar manner to the connection between the catheter linking arm 351 and the drive gear 303. The sensing element 372 is preferably a flexible sharp. Guide rails 364 and 365 in the housing 302 facilitate linear movement of the sensing element hub 371, as shown in FIG. 30.

Figure 23:
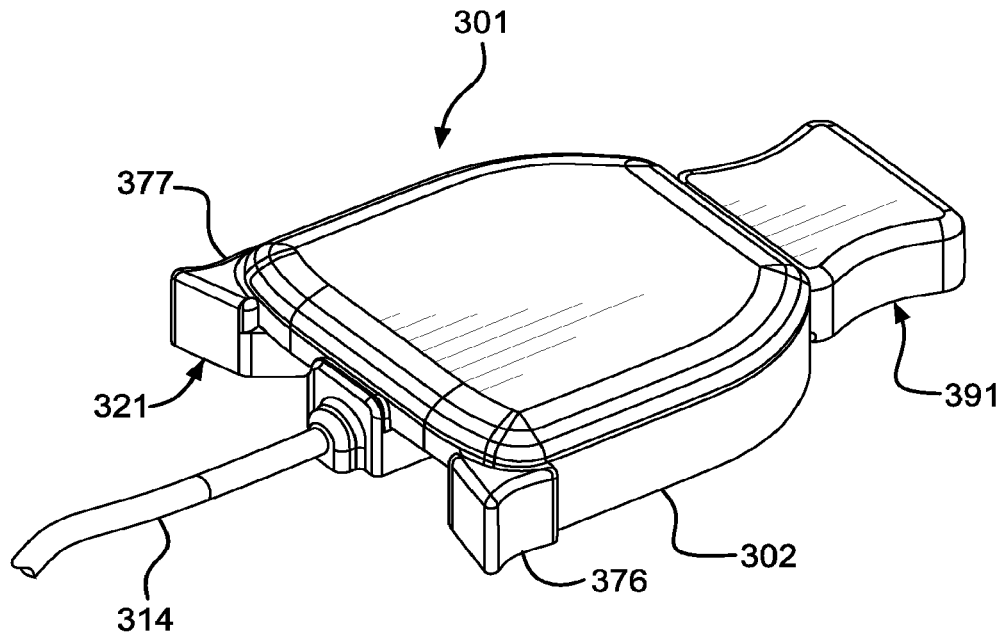
FIG. 23 is a perspective view of an infusion set with a sensing element in accordance with a third exemplary embodiment of the present invention.
Figure 24:
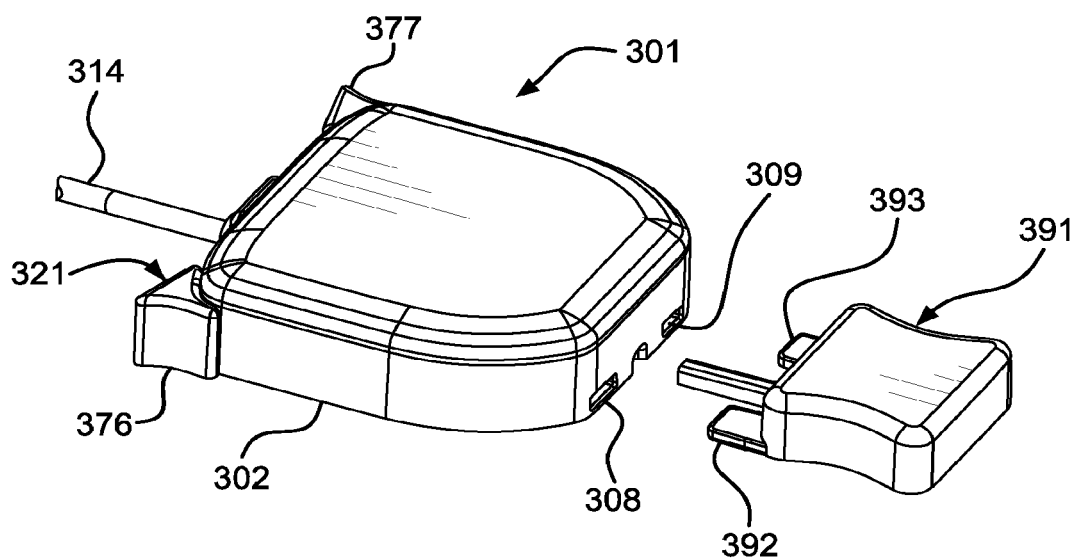
FIG. 24 is a perspective view of the infusion set of FIG. 23 with a locking member removed.

A locking member 391 has outwardly extending first and second tabs 392 and 393, as shown in FIGS. 23 and 24. The locking tabs 392 and 393 pass through openings 308 and 309 in the housing 302 and are received by recesses 310 and 311 in the drive and slave gears 303 and 304, respectively, as shown in FIG. 25. A friction fit is created between the locking tabs 392 and 393 and the openings 308 and 309 in the housing 302. The locking tabs 392 and 393 prevent rotation of the drive and slave gears 303 and 304 when the locking tabs 392 and 393 are received by the recesses 310 and 311 in the drive and slave gears 303 and 304, respectively. Removing the locking member 391, as shown in FIG. 24, disengages the tabs 392 and 393 from the drive and slave gear recesses 310 and 311, thereby allowing the torsion spring 381 to rotate the drive and slave gears 303 and 304.

Figure 29:
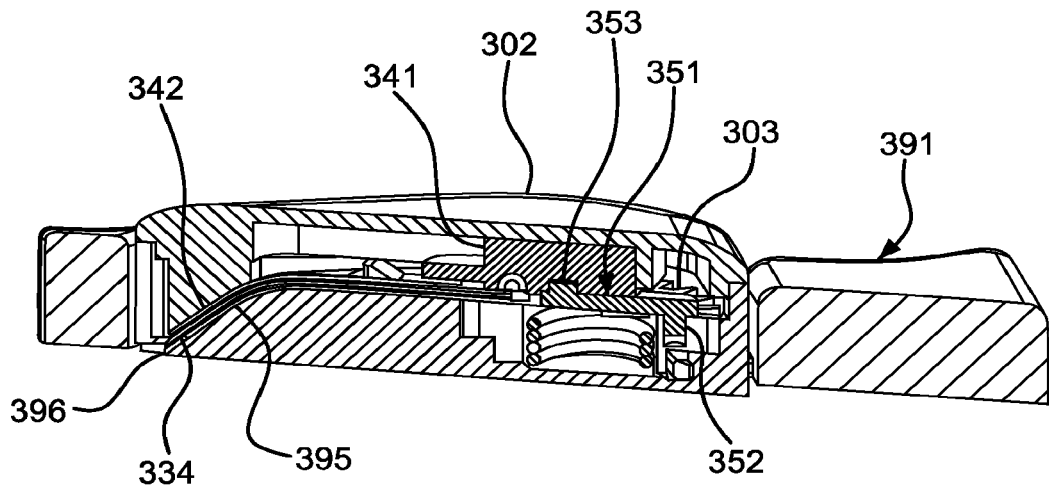
FIG. 29 is a partial perspective view in cross-section of the infusion set of FIG. 23 showing an introducer needle and catheter.

An angled guide 395 is provided in the housing 302 to guide movement of the introducer needle 334 and the catheter 342, as shown in FIG. 29. The angled guide 395 creates an angle with respect to the surface of the skin of between approximately 30 and 45 degrees, inclusive, and preferably about 45 degrees. An opening 396 is formed in the housing 302 at the end of the angled guide 395 to allow the introducer needle 334 and catheter 342 to exit the housing 302.

Figure 27:
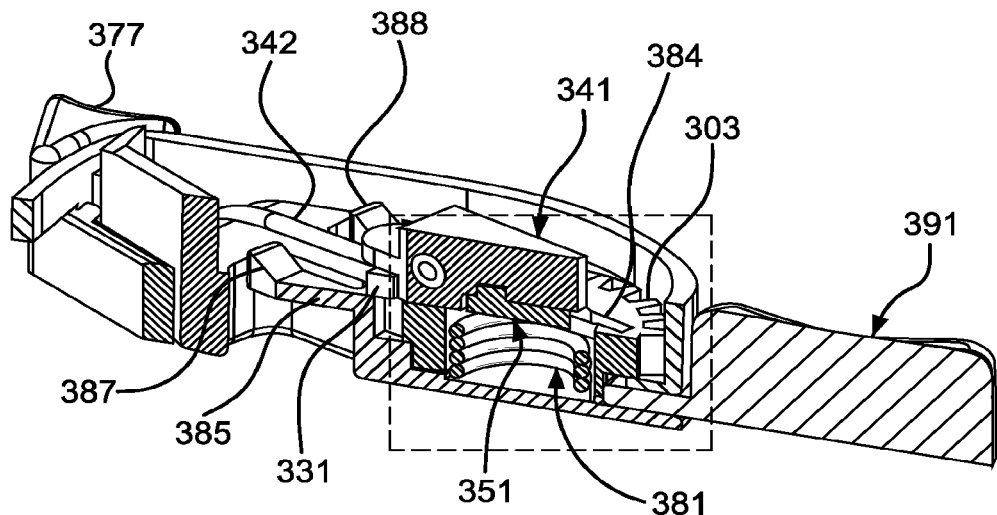
FIG. 27 is a partial perspective view of the infusion set of FIG. 23.
Figure 28:
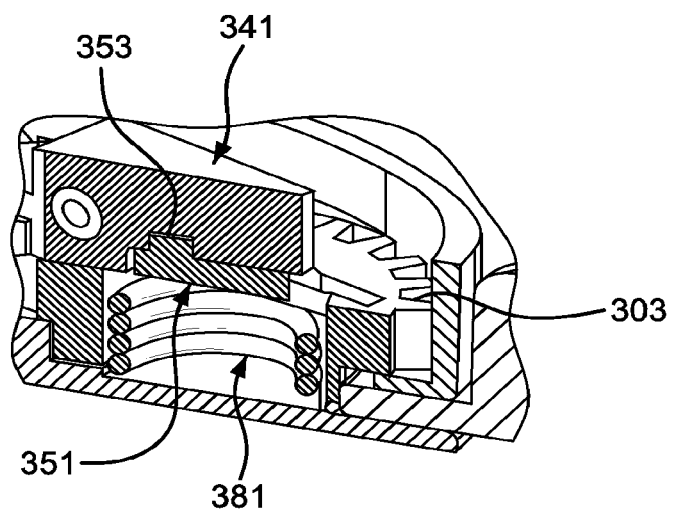
FIG. 28 is an enlarged perspective view of a linking arm of FIG. 27.
Figure 35:
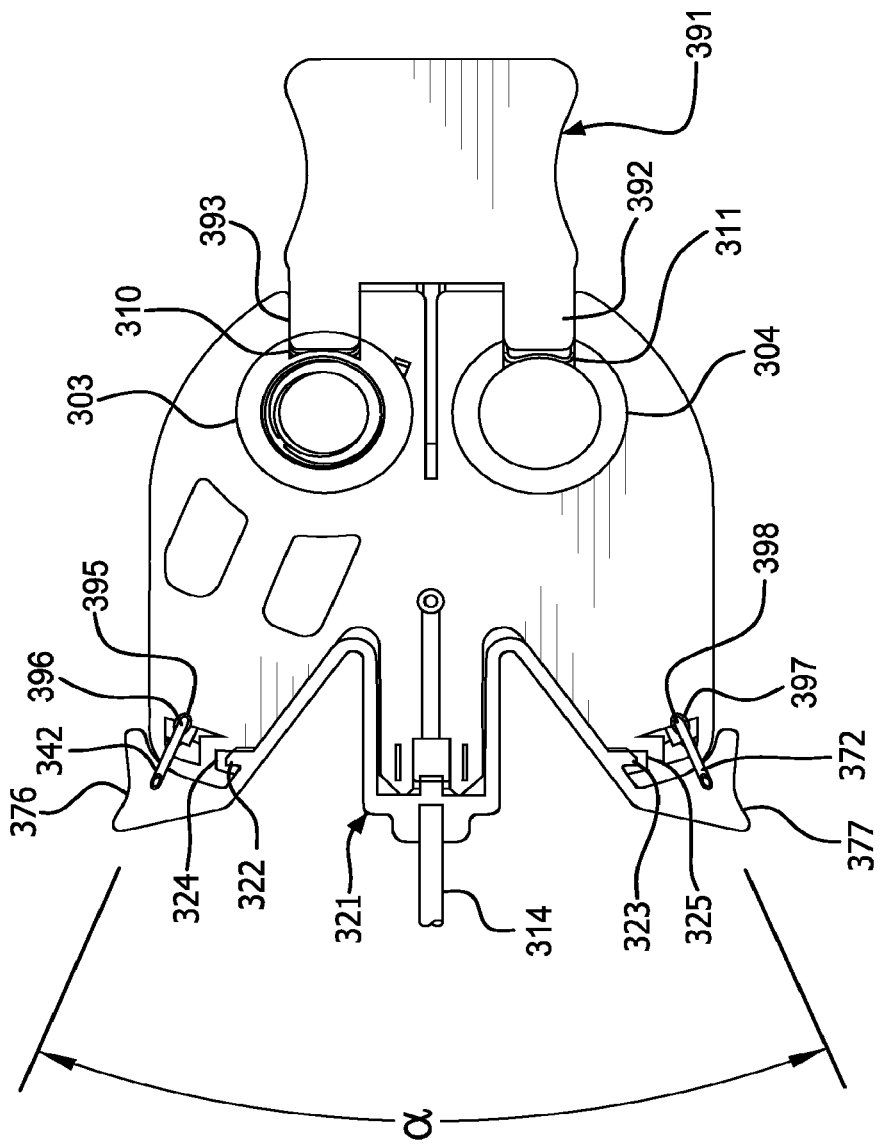
FIG. 35 is a bottom plan view of the infusion set of FIG. 23 with a cannula and sensing element exposed.

First and second flexible arms 385 and 386 extend in the housing 302 in the direction of movement of the catheter hub 331, as shown in FIGS. 26 and 27. Upwardly extending hooks 387 and 388 are disposed at an end of the flexible arms 385 and 386. A substantially similar second angled guide 397 is disposed in the housing 302 to guide the sensing element 372 through an opening 398. Preferably, the angled guides 395 and 397 are disposed at an angle α with respect to each other, as shown in FIGS. 26 and 35. The angle α is preferably approximately 45 degrees to maximize the distance between the point of entry into the skin between the catheter 342 and the sensing element 372. This minimizes the direct effect of the insulin being administered on the measured blood glucose level.

A fluid connector 321 is removable connected to the housing 302, as shown in FIGS. 23-25 and 35. Tubing 314 from the fluid connector 321 is connected to a pump (not shown) to supply medicament to the infusion set 301. A penetrating member 317 of the fluid connector 321 pierces a septum 315 disposed in the housing 302 to provide a fluid path from the pump to the infusion set 301. Tabs 322 and 323 of the fluid connector 321 are received by recesses 324 and 325 in the housing 302, as shown in FIGS. 25 and 26. Finger grips 376 and 377 of the fluid connector 321 facilitate a user's grip on the housing 302. The finger grips 376 and 377 can be squeezed together to unlock the tabs 322 and 323 from the housing recesses 324 and 325 to remove the fluid connector 321 from the housing 302.

When the infusion set is ready to be used, an adhesive backing (not shown) is removed from the housing such that the housing can be disposed on the user's body at a desired location. Finger grips 376 and 377 connected to the housing 302 facilitate the user's grip on the housing 302 while removing the locking member 391. The locking member 391 is removed from the housing 302, such that the locking tabs 392 and 393 are disengaged from the recesses 310 and 311 in the drive and slave gears 303 and 304, respectively. The drive and slave gears 303 and 304 are free to rotate after the locking tabs 392 and 393 are removed from the recesses 310 and 311.

The torsion spring 381 causes the drive gear 303 to rotate when the locking tabs 392 and 393 have been removed from the recesses 310 and 311. The introducer hub 341 and catheter hub 331 are initially in a first position, as shown in FIG. 26, proximate the drive gear 303. As the drive gear 303 rotates, the catheter linking arm 351 converts the rotation of the drive gear 303 into linear movement of the catheter introducer hub 341. The catheter linking arm 351 moves the catheter introducer hub 341 linearly away from the drive gear 303, as shown in FIG. 23. The catheter introducer hub 341 pushes the catheter hub 331 as the catheter introducer hub 341 moves away from the drive gear 303. The guide rails 354 and 355 facilitate linear movement of the catheter introducer hub 341 and catheter hub 331, as shown in FIG. 30.

Rotation of the drive gear 303 rotates the slave gear 304 due to the engagement between the drive gear teeth 306 and the slave gear teeth 307. The sensing element linking arm 361 moves the sensing element hub 371 as the slave gear 304 is rotated by the drive gear 303. The guide rails 364 and 365 facilitate linear movement of the sensing element hub 371, as shown in FIG. 30.

When the drive gear 303 has rotated approximately 180 degrees, the introducer needle 334 and the catheter 342 have exited the housing 302 and are inserted in the skin in a substantially similar manner as in the first and second exemplary embodiments. Substantially simultaneously, the sensing element 372 has exited the housing 302 and is inserted in the skin in a substantially similar manner to the introducer needle 334.

Figure 33:
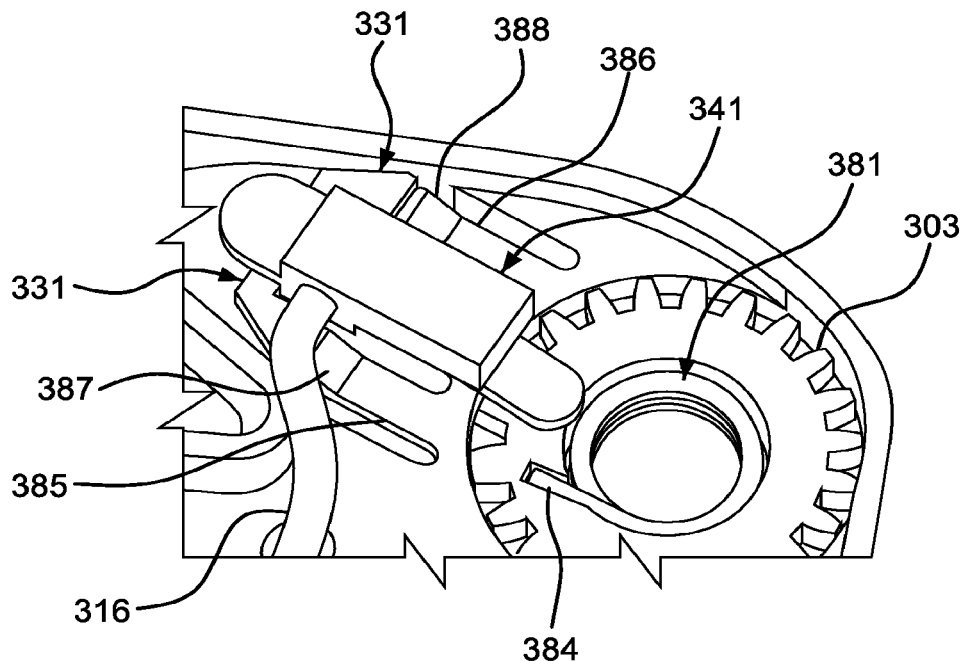
FIG. 33 is a perspective view of the infusion set of FIG. 23 showing catheter and introducer hubs in a first position.
Figure 34:
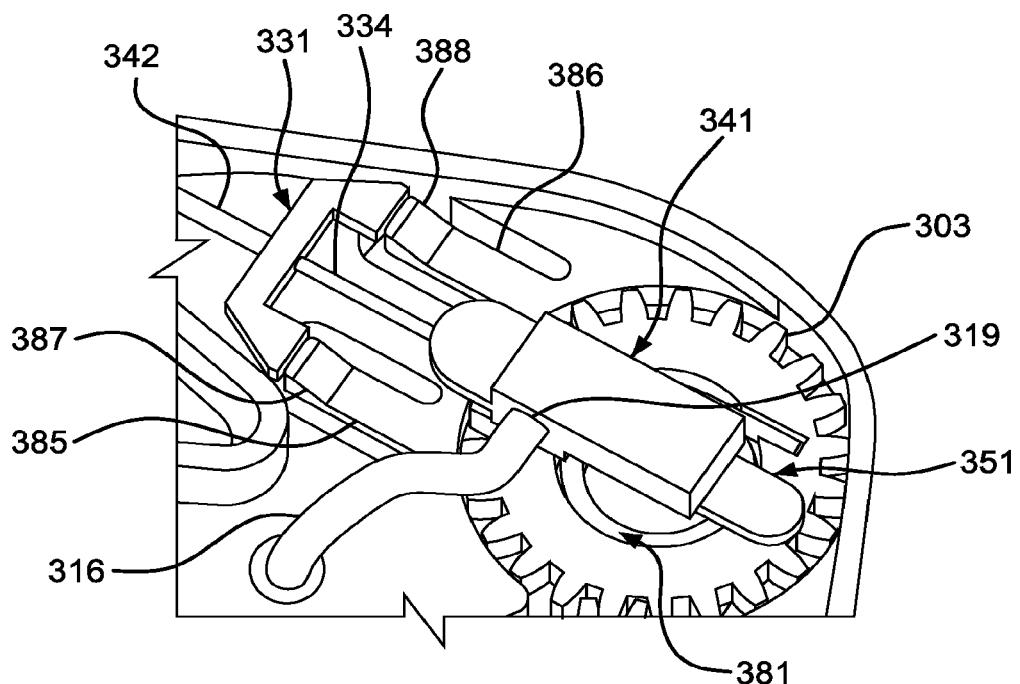
FIG. 34 is a perspective view of the infusion set of FIG. 23 showing the catheter hub in a second position and the introducer hub returned to the first position.

The torsion spring 381 continues to rotate the drive gear 303. The linking arm 351 moves the introducer hub 341 rearwardly, thereby withdrawing the introducer needle 334. The catheter hub 331 has passed over the hooks 387 and 388 at the end of the flexible arms 385 and 386 and is prevented from rearward movement by the hooks 387 and 388, as shown in FIGS. 33 and 34.

After having rotated approximately 180 degrees, the slave gear teeth 307 are not engaged with the drive gear teeth 306. Accordingly, the sensing element linking arm 362 is not moved and the sensing element hub 371 is not moved such that the sensing element 372 remains inserted in the skin.

Figure 31:
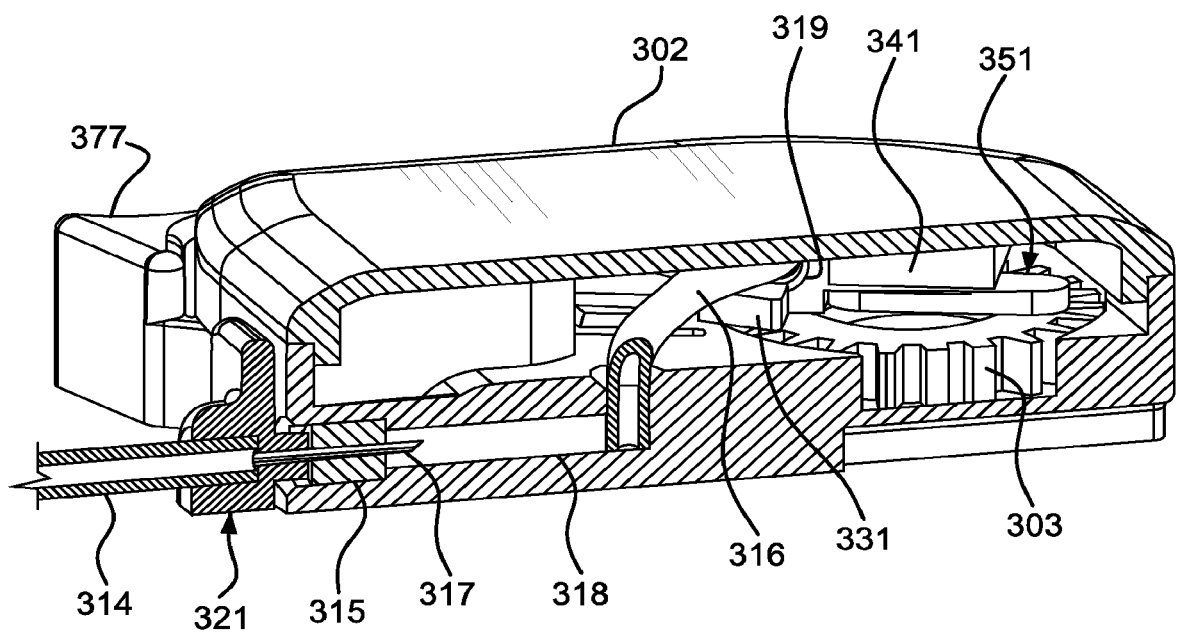
FIG. 31 is a partial perspective view in cross-section of the infusion set of FIG. 23 showing a fluid path.
Figure 32:
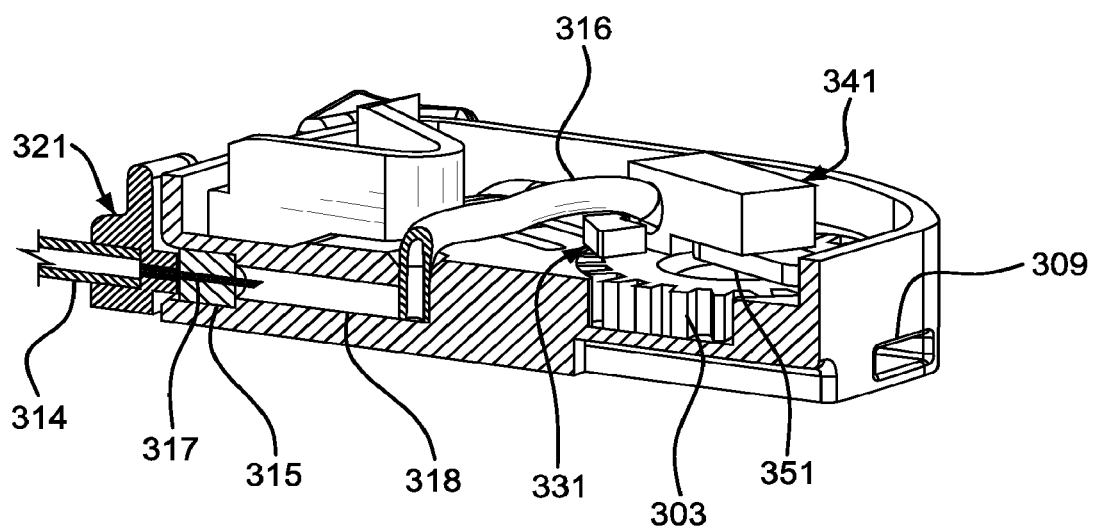
FIG. 32 is another partial perspective view in cross-section of the infusion set of FIG. 31 showing a fluid path.

Tubing 314 extends from the fluid connector 321 and is adapted to connect to a pump. The tubing 314 is connected to the penetrating member 317 extending from an end of the tubing 314. The penetrating member 317 is adapted to penetrate the septum 315 disposed in the housing 302, as shown in FIGS. 31 and 32. The septum 315 seals a fluid channel 318 disposed in the housing 302. A flexible base tubing 316 is disposed at an opposite end of the fluid channel 318 from the septum 315. An opposite end of the flexible base tubing 316 is connected to an opening 319 in the introducer hub 341. A fluid path is created from the connector tubing 314, through the septum 315, through the fluid channel 318, through the base tubing 316 and into the introducer hub 341, through the introducer needle 334 and into the catheter 342, as shown in FIGS. 31 and 32. The base tubing 316 is flexible such that the base tubing 316 moves with the introducer hub 341 between first and second positions, as shown in FIGS. 26, 33 and 34. The tubing 314 can be removed from the housing 302 by squeezing the finger grips together 376 and 377 to unlock the tabs 322 and 323 from the housing recesses 324 and 325.

The exemplary embodiment described above can be adapted for use with either intradermal or subcutaneous injections. In addition, a different method of maintaining the fluid connection is possible other than using the tube 314, such as a sliding seal. Alternative methods can be used for connecting and disconnecting the fluid connector 321 to and from the housing 302, and for connecting and disconnecting the locking member 391 to and from the housing 302, such as a button or a dial.

Although the exemplary embodiment described above is an infusion set, it will be apparent to those of ordinary skill in the art that the principles of the present invention are also applicable to patch pumps (self-contained infusion devices with integral reservoirs and pumping mechanisms) and other types of medical infusion and injection devices.

Fourth Exemplary Embodiment

The fourth exemplary embodiment of an infusion set 401, as shown in FIGS. 36-39, is substantially similar to the infusion set 301 of the third exemplary embodiment shown in FIGS. 23-35. Similar components are identified with the same base number in the 400 series, e.g., 4xx. The sensing element 472 is inserted by a sensing element introducer needle in a similar manner as the catheter 342 of the third exemplary embodiment, instead of the sensing element itself being a sharps. The remaining operation and structure of the infusion set 401 is substantially similar to the infusion set 301 of the third exemplary embodiment.

A locking member 491 is received in the housing recesses such that a friction fit is created therebetween. When the infusion set 401 is ready to be used, adhesive backing is removed from the housing 402 such that the housing can be disposed on the user's body at a desired location. Finger grips 476 and 477 connected to the housing 402 facilitate the user's grip on the housing 402 while removing the locking member 491. The locking member 491 is removed from the housing 402, such that the locking tabs are disengaged from the recesses in the drive and slave gears 403 and 404, respectively. The drive and slave gears 403 and 404 are free to rotate after the locking tabs are removed from the drive and slave gear recesses and from the openings in the housing 402.

Figure 36:
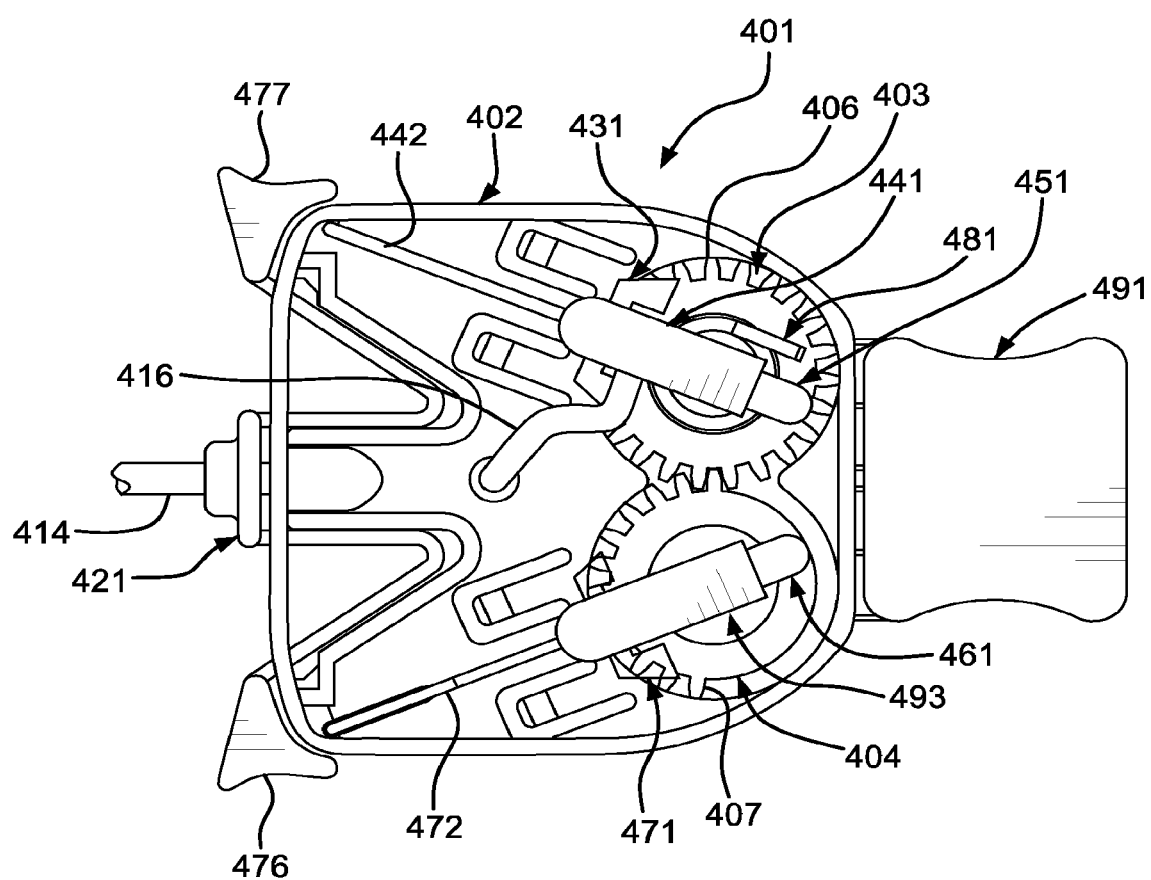
FIG. 36 is partial a top plan of an infusion set in accordance with a fourth exemplary embodiment showing an infusion set having two sets of hubs.
Figure 37:
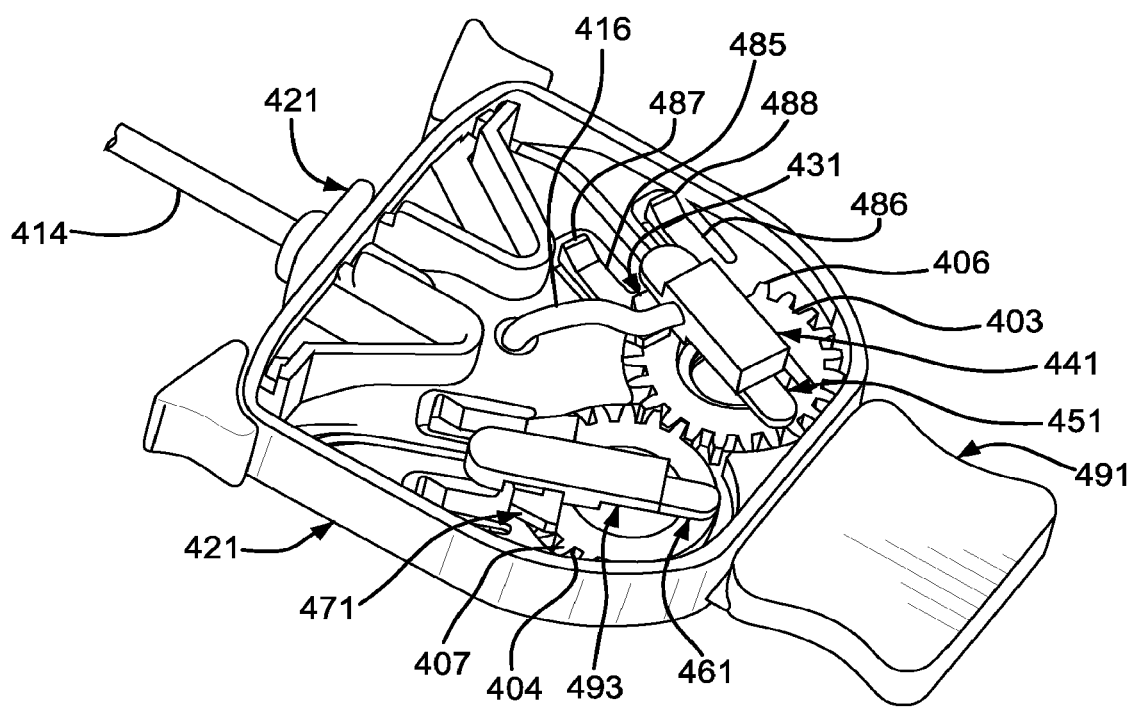
FIG. 37 is a partial perspective view of the infusion set of FIG. 35.

The torsion spring 481 causes the drive gear 403 to rotate when the locking tabs have been removed from the recesses in the drive and slave gears 403 and 404. The introducer hub 441 and catheter hub 431 are initially in a first position, as shown in FIGS. 36 and 37, proximate the drive gear 403. As the drive gear 403 rotates, the catheter linking arm 451 converts the rotation of the drive gear 403 into linear movement of the catheter introducer hub 441. The catheter linking arm 451 moves the catheter introducer hub 441 linearly away from the drive gear 403. The catheter introducer hub 441 pushes the catheter hub 431 as the catheter introducer hub 441 moves away from the drive gear 403. The guide rails in the housing 402 facilitate linear movement of the catheter introducer hub 441 and catheter hub 431.

Rotation of the drive gear 403 rotates the slave gear 404 due to the engagement between the drive gear teeth 406 and the slave gear teeth 407. The sensing element linking arm 461 moves the sensing element introducer hub 493 as the slave gear 404 is rotated by the drive gear 403. The sensing element introducer hub 493 pushes the sensing element hub 471 as the sensing element introducer hub 493 moves away from the slave gear 404. The guide rails in the housing 402 facilitate linear movement of the sensing element introducer hub 493 and the sensing element hub 471.

When the drive gear 403 has rotated approximately 180 degrees, the introducer needle and the catheter 442 have exited the housing 402 and are inserted in the skin in a substantially similar manner as in the first, second and third exemplary embodiments. Substantially simultaneously, the sensing element 472 has exited the housing 402 and is inserted in the skin in a substantially similar manner as the introducer needle.

The torsion spring 481 continues to rotate the drive gear 403. The linking arm 451 moves the introducer hub 441 rearwardly, thereby withdrawing the introducer needle. The catheter hub 431 has passed over the hooks 487 and 488 at the end of the flexible arms 485 and 486 and is prevented from rearward movement by the hooks 487 and 488.

Figure 38:
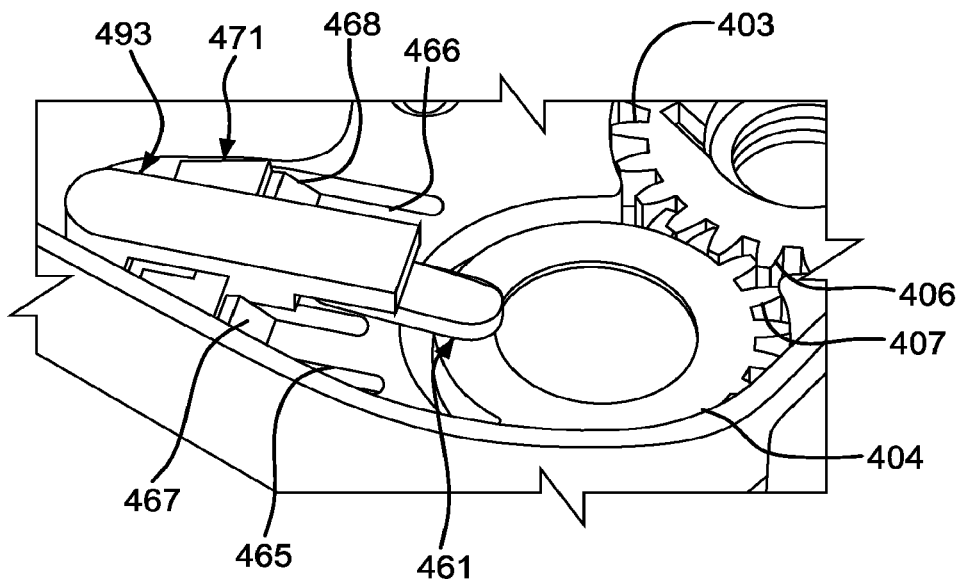
FIG. 38 is a partial perspective view of the infusion set of FIG. 35 showing the hub set connected to a slave gear.
Figure 39:
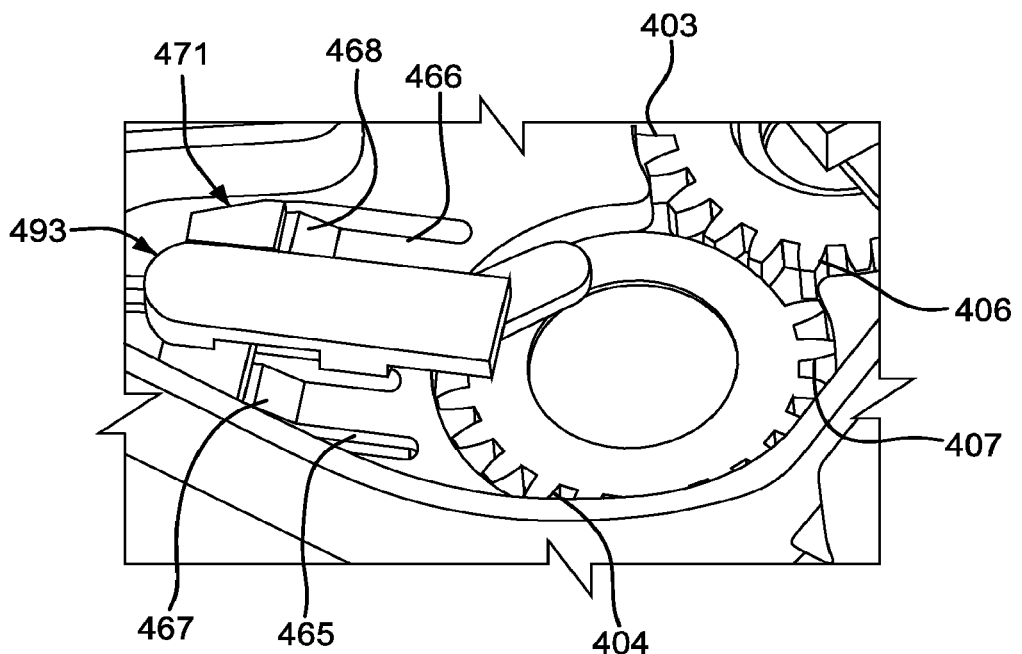
FIG. 39 is a partial perspective view of the infusion set of FIG. 35 showing an introducer hub in a second position and a sensing element hub slightly withdrawn from the second position.

After having rotated approximately 180 degrees, the slave gear teeth 406 are still engaged with the drive gear teeth 406 as the slave gear teeth 407 extend approximately 210 degrees around the outer perimeter of the slave gear 404, as shown in FIGS. 36 and 37. Accordingly, the slave gear 404 is rotated approximately 30 degrees, such that the linking arm 461 draws the sensing element introducer hub 493 rearwardly. The sensing element hub 471 is prevented from rearward movement by hooks 467 and 468 at the end of flexible arms 465 and 466, as shown in FIGS. 38 and 39. The rearward movement of the sensing element introducer hub 493 retracts the sensing element introducer needle, thereby exposing the sensing element (similar to the catheter being exposed in the previous exemplary embodiments). For example, the 30 degree rotation of the slave gear 404 slightly retracts the sensing element introducer needle to expose the tip and a small length (e.g., approximately 2 mm) of the sensing element 472. Once the slave gear teeth 407 are no longer engaged with the drive gear teeth 406, as shown in FIG. 39, the sensing element introducer hub 493 is no longer moved rearwardly.

The exemplary embodiment described above can be adapted for use with either intradermal or subcutaneous injections. Although the exemplary embodiment described above is an infusion set, it will be apparent to those of ordinary skill in the art that the principles of the present invention are also applicable to patch pumps (self-contained infusion devices with integral reservoirs and pumping mechanisms) and other types of medical infusion and injection devices.

Fifth Exemplary Embodiment

Figure 40:
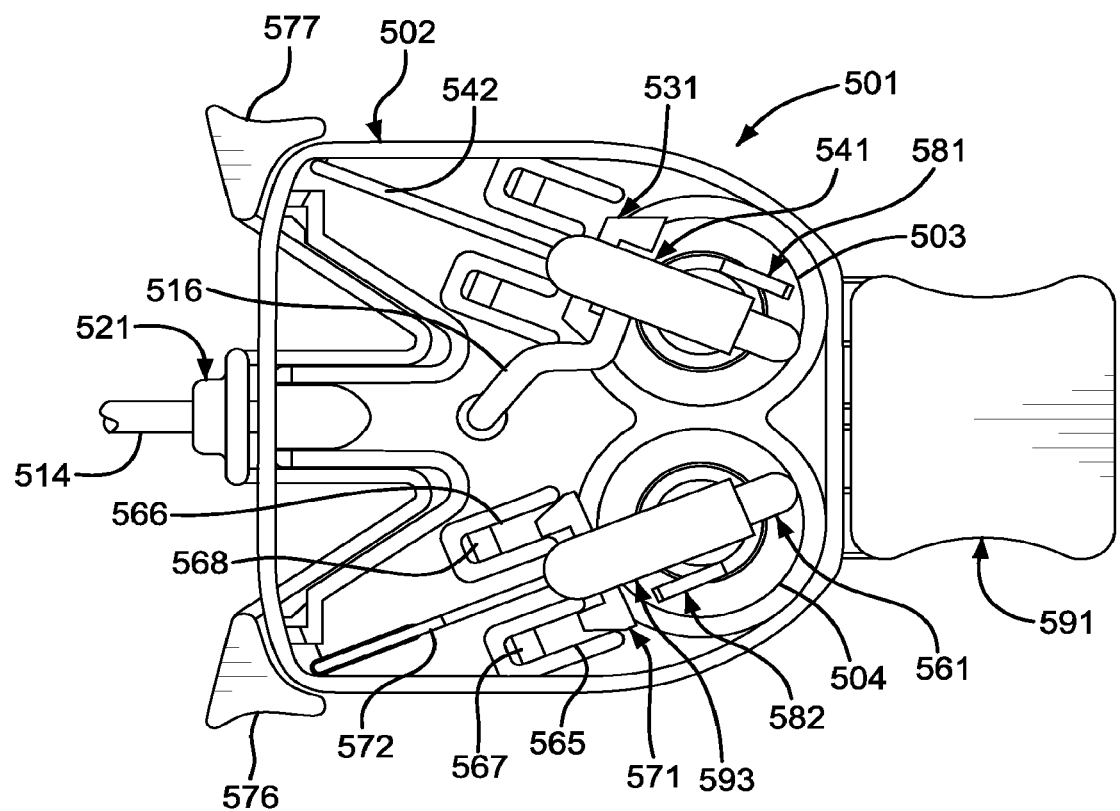
FIG. 40 is a partial top plan view of an infusion set in accordance with a fifth exemplary embodiment of the present invention.

The fifth exemplary embodiment of an infusion set 501, as shown in FIG. 40, is substantially similar to the infusion sets 301 and 401 of the third and fourth exemplary embodiments shown in FIGS. 23-39. Similar components are identified with the same base number in the 500 series, e.g., 5xx. The sensing element 572 is inserted by a sensing element introducer needle in a similar manner as in the fourth exemplary embodiment. Instead of using a slave gear, the sensing element introducer hub 593 and the sensing element hub 571 are independently driven by a second torsion spring 582.

A first torsion spring 581 drives the catheter introducer hub 541 and the catheter hub 531 as in the previous exemplary embodiments.

The second torsion spring 582 separately drives the sensing element introducer hub 593 and the sensing element hub 571 in a substantially similar manner to the first torsion spring 581.

The infusion set 501 preferably is packaged in a sterile manner with an infusion pump (not shown) already connected to the tubing 514. A locking member 591 is received in the housing recesses such that a friction fit is created therebetween. When the infusion set 501 is ready to be used, an adhesive backing (not shown) is removed from the housing 502 such that the housing can be disposed on the user's body at a desired location. Finger grips 576 and 577 connected to the housing 502 facilitate the user's grip on the housing 502 while removing the locking member 591. The locking member 591 is removed from the housing 502, such that the locking tabs are disengaged from the recesses in the first and second drive discs 503 and 504, respectively. The first and second drive discs 503 and 504 are free to rotate after the locking tabs are removed from the first and second drive disc recesses and from the openings in the housing 502.

The second torsion spring 581 causes the second drive disc 505 to rotate when the locking tabs have been removed from the recesses in the first and second drive discs 503 and 504. The sensing element introducer hub 593 and sensing element hub 571 are initially in a first position, as shown in FIG. 40, proximate the second drive disc 504. As the second drive disc 504 rotates, the sensing element linking arm 561 converts the rotation of the second drive disc 504 into linear movement of the sensing element introducer hub 593. The sensing element linking arm 561 moves the sensing element introducer hub 593 linearly away from the second drive disc 504. The sensing element introducer hub 593 pushes the sensing element hub 571 as the sensing element introducer hub 593 moves away from the second drive disc 504. The guide rails in the housing 502 facilitate linear movement of the sensing element introducer hub 593 and the sensing element hub 571.

When the second drive disc 504 has rotated approximately 180 degrees, the introducer needle and the sensing element 572 have exited the housing 502 and are inserted in the skin in a substantially similar manner as in the first, second, third and fourth exemplary embodiments. Substantially simultaneously, the catheter 542 and catheter introducer needle have exited the housing 502 and are inserted in the skin.

The second torsion spring 582 continues to rotate the second drive disc 504. The sensing element linking arm 561 moves the sensing element introducer hub 593 rearwardly, thereby withdrawing the sensing element introducer needle. The sensing element 572 remains inserted under the surface of the skin. The sensing element hub 571 has passed over the hooks 567 and 568 at the end of the flexible arms 565 and 566 and is prevented from rearward movement by the hooks 567 and 568.

The second torsion spring 582 can be set to a different deflection ratio than the first torsion spring 581. For example, the first torsion spring 581 can be set for 180 degrees of travel, such that the first 90 degrees inserts the catheter introducer needle and catheter 542 and the second 90 degrees retracts the catheter introducer needle into the housing 502. The second torsion spring 582 can be set for 120 degrees of travel. The first 90 degrees inserts the sensing element introducer needle and sensing element 572. The remaining 30 degrees of travel slightly retracts the sensing element introducer needle to expose the tip and a small length (e.g., approximately 2 mm) of the sensing element 572.

The exemplary embodiment described above can be adapted for use with either intradermal or subcutaneous injections. Although the exemplary embodiment described above is an infusion set, it will be apparent to those of ordinary skill in the art that the principles of the present invention are also applicable to patch pumps (self-contained infusion devices with integral reservoirs and pumping mechanisms) and other types of medical infusion and injection devices.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the appended claims and their equivalents.

What is claimed is:

1. An infusion device, comprising:
   a base;
   a flexible catheter movable from a first catheter position disposed substantially entirely within said base to a second catheter position in which a free end of said catheter is disposed externally of said base;
   an introducer needle located within said catheter and movable between a first introducer needle position disposed substantially entirely within said base and a second introducer needle position in which a free end of said introducer needle is disposed externally of said base;
   a torsion spring for moving said catheter from said first to said second catheter position and said introducer needle from said first to said second introducer needle position to facilitate insertion of said catheter, said introducer needle thereafter being moved by said torsion spring back toward said first introducer needle position to store said introducer needle within said base with said free end of said catheter remaining disposed externally of said base; and
   a mechanical linkage for coupling said torsion spring to said introducer needle, said mechanical linkage comprising a first member coupled to and rotated by said torsion spring and a second member coupled to said first member and to said introducer needle, the coupling between said first and second members being at fixed points on each of said first and second members.

2. The infusion device of claim 1, wherein said torsion spring is preloaded.

3. The infusion device of claim 1, wherein said first member comprises a disc.

4. The infusion device of claim 1, wherein said second member comprises a linking arm.

5. The infusion device of claim 1, wherein said first member comprises a disc and said second member comprises a linking arm.

6. The infusion device of claim 1, wherein:
   said introducer needle is carried by an introducer hub; and
   said second member is coupled to said to said introducer needle via said introducer hub.

7. The infusion device of claim 1, wherein said first member and said second member together form a rotary crank mechanism for converting rotary motion from said torsion spring to linear motion of said introducer needle.

8. The infusion device of claim 1, wherein:
   said wherein said first member comprises a first gear; and
   a second gear is engaged with said first gear to move a sensing element from a first position stored within said base to a second position external to said base.

9. The infusion device of claim 1, wherein said torsion spring is activated by a button movably connected to said base.

10. The infusion device of claim 1, wherein:
    a fluid connector is removably connected to said base; and
    said torsion spring is activated by movement of said fluid connector.

11. The infusion device of claim 1, wherein
    a second torsion spring is activated to move a sensing element from a first position stored within said base to a second position external to said base.

12. The infusion device of claim 1, wherein said movements of said catheter and said introducer needle occur at a non-perpendicular angle with respect to said base, and wherein said torsion spring has an axis substantially perpendicular to said base.

13. The infusion device of claim 1, wherein said torsion spring is activated by the release of a locking device.

* * * * *